(12) United States Patent
Drake et al.

(10) Patent No.: US 8,298,209 B2
(45) Date of Patent: Oct. 30, 2012

(54) SEALING FOR MEDICAL DEVICES/INSTRUMENTS

(75) Inventors: Ronald A. Drake, St. Louis Park, MN (US); Stanten C. Spear, Arden Hills, MN (US); Lester O. Stener, Blaine, MN (US); Gary R. Fiedler, Forest Lake, MN (US); Scott W. Hayden, Maple Grove, MN (US); Kendra Yasger, Big Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 166 days.

(21) Appl. No.: 12/848,039

(22) Filed: Jul. 30, 2010

(65) Prior Publication Data
US 2012/0029474 A1 Feb. 2, 2012

(51) Int. Cl.
*A61M 25/00* (2006.01)
(52) U.S. Cl. .................................................. 604/523
(58) Field of Classification Search .............. 604/533, 604/534, 535, 536, 537
See application file for complete search history.

(56) References Cited

U.S. PATENT DOCUMENTS

| | | | |
|---|---|---|---|
| 4,610,665 A | 9/1986 | Matsumoto et al. | |
| 4,673,393 A | 6/1987 | Suzuki et al. | |
| 5,312,355 A | 5/1994 | Lee | |
| 5,324,271 A * | 6/1994 | Abiuso et al. | 604/167.03 |
| 5,336,192 A | 8/1994 | Palestrant | |
| 5,409,463 A | 4/1995 | Thomas et al. | |
| 5,478,331 A | 12/1995 | Heflin et al. | |
| 5,782,505 A | 7/1998 | Brooks et al. | |
| 2002/0077685 A1 | 6/2002 | Sundquist et al. | |
| 2002/0177814 A1* | 11/2002 | Meng et al. | 604/164.07 |
| 2007/0293845 A1 | 12/2007 | Leeflang et al. | |
| 2012/0029421 A1* | 2/2012 | Drake et al. | 604/22 |
| 2012/0029474 A1* | 2/2012 | Drake et al. | 604/523 |
| 2012/0029480 A1* | 2/2012 | Drake et al. | 604/533 |
| 2012/0029482 A1* | 2/2012 | Drake et al. | 604/535 |

FOREIGN PATENT DOCUMENTS

| | | |
|---|---|---|
| EP | 0455215 A2 | 11/1991 |
| GB | 2387333 A | 10/2003 |
| WO | 2007133845 A2 | 11/2007 |

OTHER PUBLICATIONS (PCT/US2011/045943) PCT Notification of Transmittal of the International Search Report and the Written Opinion of the International Searching Authority, Mailed Oct. 25, 2011, 9 pages.

* cited by examiner

*Primary Examiner* — Theodore Stigell
*Assistant Examiner* — Aarti B Berdichevsky
(74) *Attorney, Agent, or Firm* — Reed A. Duthler

(57) ABSTRACT

A seal member for assembly within, or a seal zone portion of, a lumen of a medical instrument/device includes a slit segment and a bore, wherein the slit segment intersects with a funnel-like segment of the bore.

11 Claims, 15 Drawing Sheets

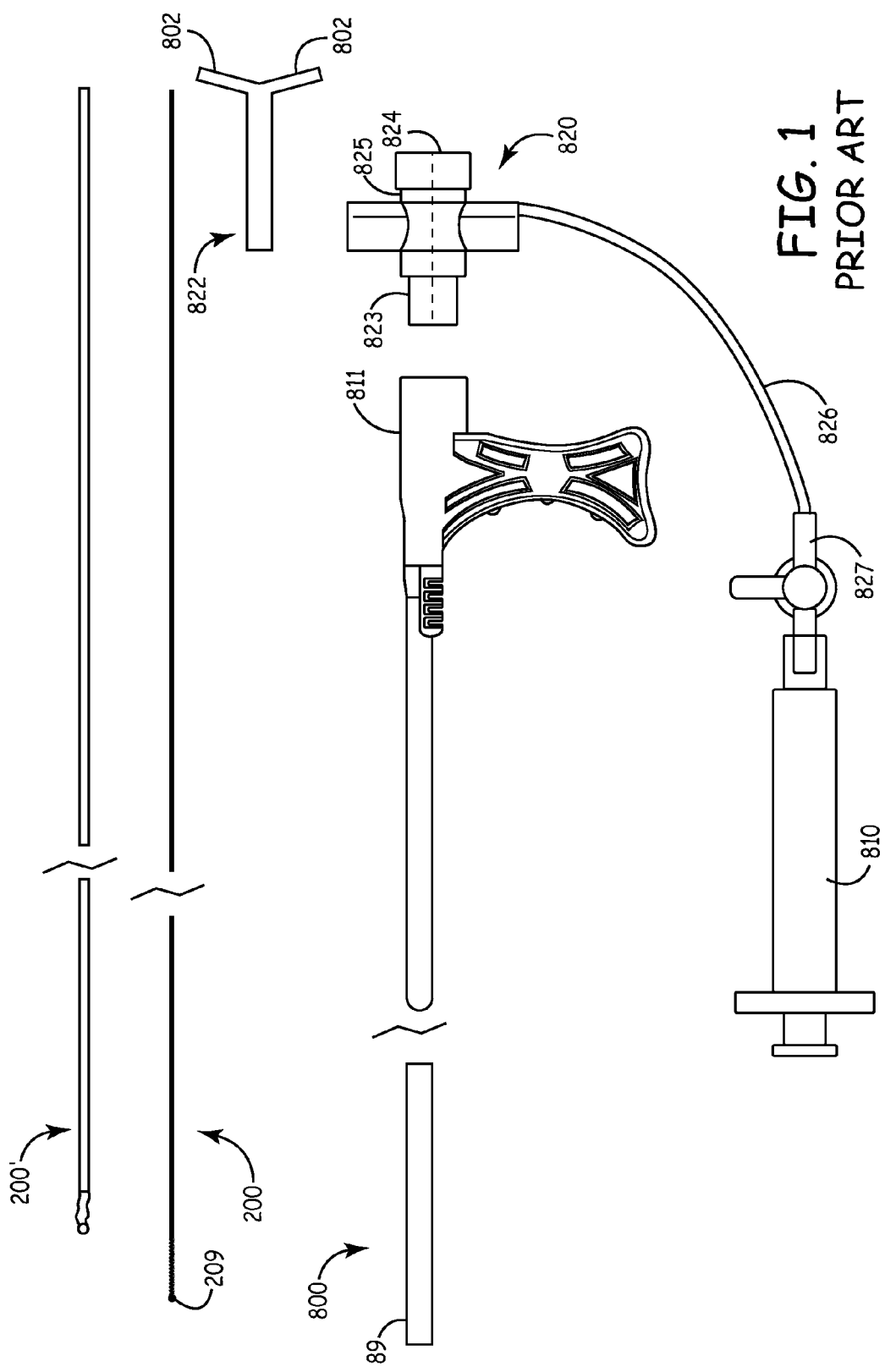

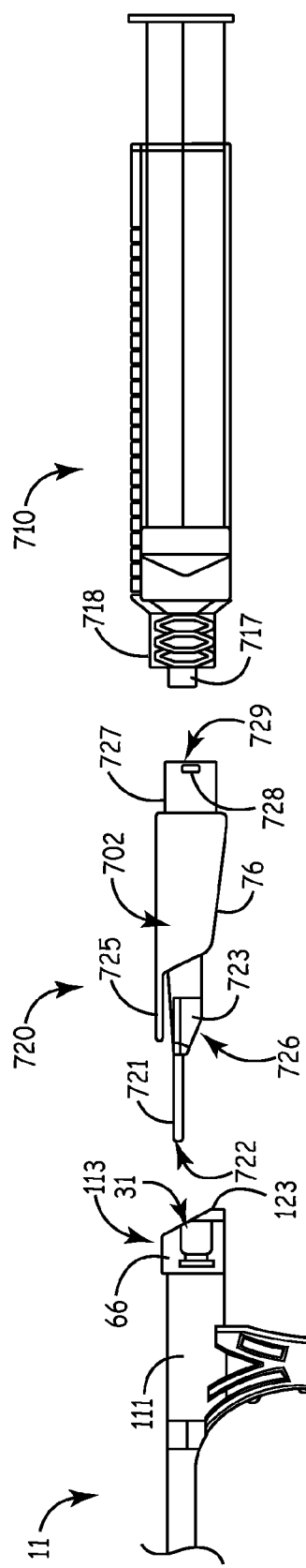
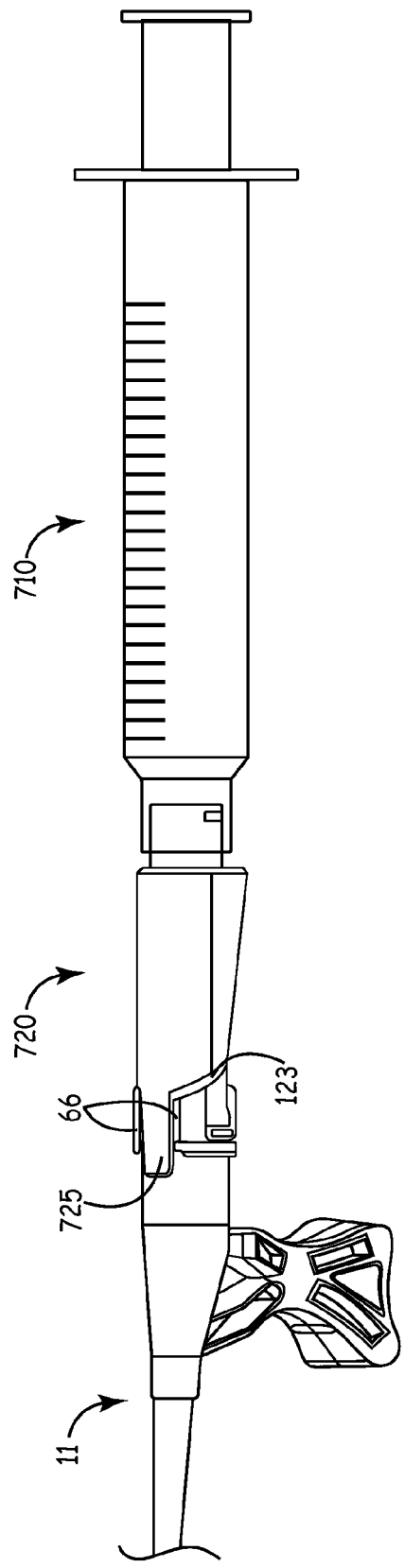
FIG. 7A
FIG. 7B

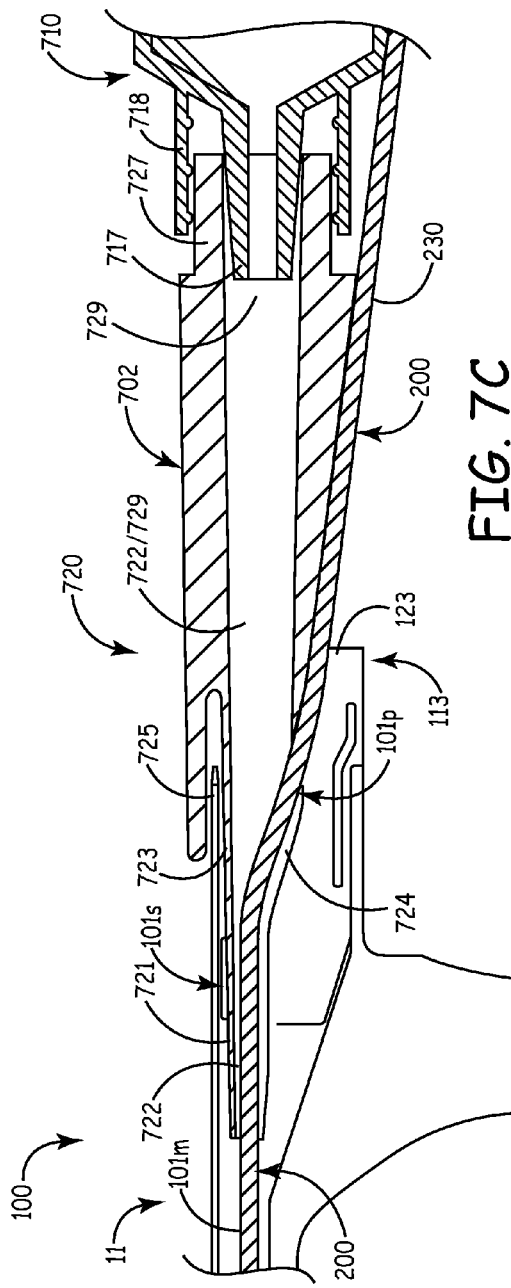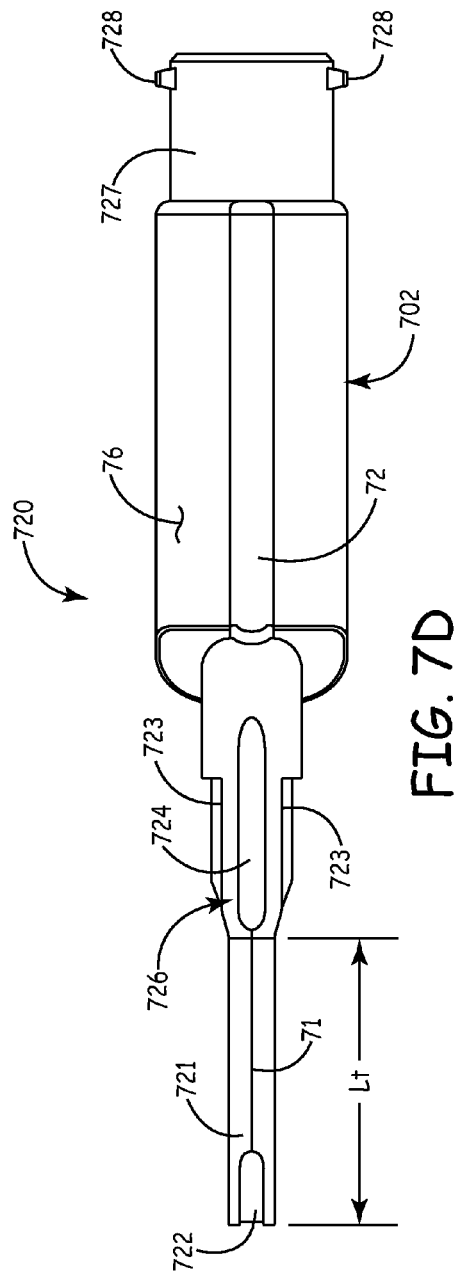
FIG. 7C
FIG. 7D

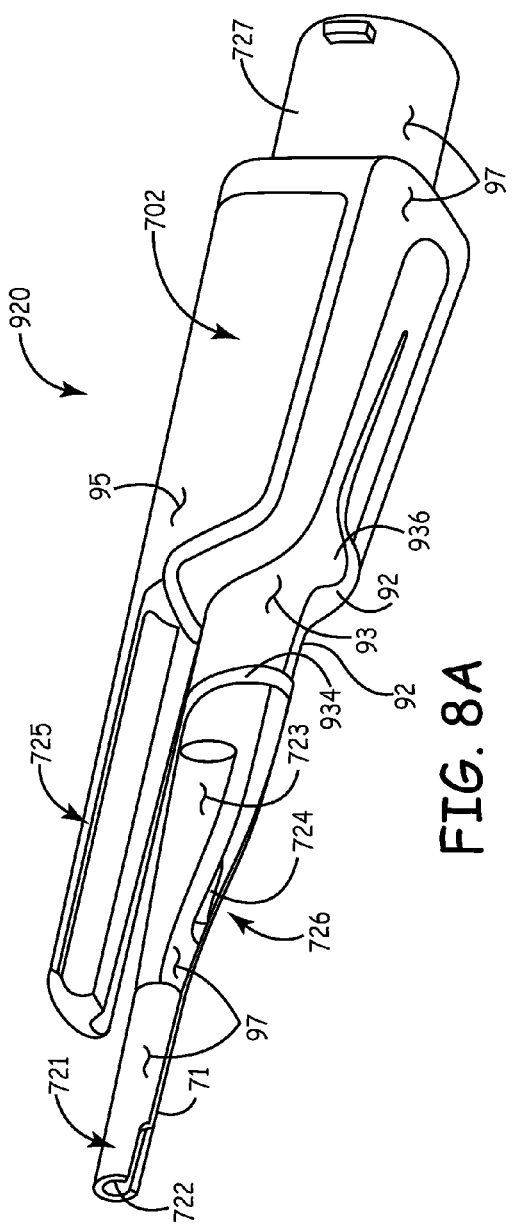
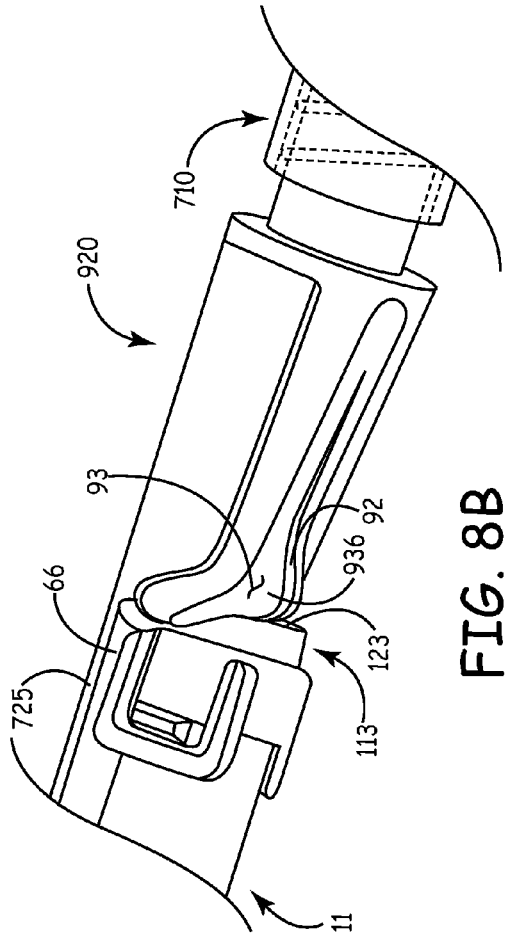
FIG. 8A
FIG. 8B

SEALING FOR MEDICAL DEVICES/INSTRUMENTS

RELATED APPLICATIONS

The present application is related to three co-pending and concurrently-filed applications, all of which are hereby incorporated by reference, in their entireties, and which have the following titles and Serial Numbers: MEDICAL DELIVERY SYSTEMS AND APPARATUS—Ser. No. 12/848,044; TOOLS AND METHODS RELATED TO CATHETER DELIVERY—Ser. No. 12/848,029; and CATHETER APPARATUS—Ser. No. 12/848,054.

TECHNICAL FIELD

The present invention pertains to apparatus for positioning/delivering medical devices/instruments within a body of a patient.

BACKGROUND

Various types of catheters and associated methods for the delivery of medical devices/instruments to target sites within a patient's body are known in the art. A properly positioned catheter can provide a convenient conduit for an operator/clinician to pass an elongate medical device, such as a medical electrical lead, into the body in order to deliver a site specific therapy from the device. However, the task of preventing excessive leakage/backflow of bodily fluids, for example, blood, and/or other procedure-related fluids out from a positioned catheter can, at times, somewhat complicate catheter delivery procedures.

With reference to FIG. 1, a portion of a catheter delivery system, which is known in the art, is shown. FIG. 1 illustrates the system including a catheter 800, a sealing assembly 820, a syringe 810, a relatively smaller diameter guide wire 200, a relatively larger diameter guide wire 200' and an insertion accessory tool 822, for example, to assist in inserting devices/instruments, such as guide wires 200/200', a medical electrical lead and a sub-selecting catheter, into catheter 800. An example of the illustrated catheter 800 is the Attain Command® Catheter, available from Medtronic, Inc., and examples of the illustrated guide wires 200/200' can be any of the many suitable guide wires known to those skilled in the art; an example of the sealing assembly 820 and associated insertion tool 822 is the SafeSheath® Sealing Adapter and associated Transvalvular Insertion Tool, available from Pressure Products. According to FIG. 1, sealing assembly 820 is connected to catheter 800 by inserting a distal end 823 of assembly 820 into a hub 811 of catheter 800, and, once connected, a valve/seal member (for example, like that described in U.S. Pat. Nos. 5,125,904, 5,312,355 and 5,409,463), which is located within a body 825 of assembly 820, in proximity to a proximal end 824 thereof, both seals off a lumen of catheter 800 and provides a passageway into the lumen. This passageway, into the lumen of catheter 800, is intended to allow passage of a medical device, for example, a medical electrical lead, therethrough, so that the operator may deliver the device, through the lumen of catheter 800, to a target site, within a body of a patient. The valve/seal member of assembly 820 is designed to seal around the device as it passes therethrough and thereby prevent an excessive volume of bodily fluids from leaking out from proximal end 824, and the design thereof is such that tool 822 is typically required to provide passage therethrough for the device.

The valve/seal member may further seal about a dilator device (not shown), which facilitates introduction of catheter 800 into the patient's venous system via a venous access site. Larger diameter guide wire 200', for example, having a 0.035 inch diameter, may be used to gain initial access and the dilator, having a uniform inner diameter provides a passageway through the valve/seal member as the operator introduces catheter 800 over guide wire 200', in order to position distal end 89 of catheter within the venous system, according to methods known in the art, prior to delivering the medical device through the lumen. Smaller diameter guide wire 200, for example, having a diameter of approximately 0.014 inch, may be used to facilitate the delivery of the device. Upon removal of the dilator and the larger diameter guide wire 200', smaller diameter guide wire 200 may be loaded into the lumen of catheter 800 from proximal end 824 of sealing assembly 820, wherein insertion tool 822 may be necessary to facilitate insertion of a distal tip 209 of guide wire 200, which is typically somewhat floppy and deformable, through the valve/seal member of assembly 820. Tool 822 is a disposable tubular member that is easily peeled away from around loaded guide wire 200, by pulling apart ends 802. Alternately, if a guide wire is not employed, tool 822 may assist in inserting a medical device, such as an electrical lead, into the lumen of catheter 800, after which, tool 822 may be peeled away from around the inserted device.

FIG. 1 further illustrates sealing assembly 820 including a side tubing port 826 extending to a stopcock 827, which is coupled to syringe 810; tubing port 826 provides a passageway for the injection of a fluid from syringe 810 into the lumen of catheter 800, downstream or distal of the valve/seal member of valve assembly 820. The fluid may be a saline flush or a radiopaque contrast agent that is useful for visualizing anatomy, for example, a venous anatomy on fluoroscopy, which is downstream of distal end 89 of catheter 800, and thereby facilitate the positioning of distal end 89, guidewire 200 and/or the medical device at, or in proximity to a target site. Thus, the valve/seal member of assembly 820 must also prevent backflow of the fluid injected from syringe 810 around both guide wire 200 and the medical device, which are either together or individually inserted through the valve/seal member.

Once the medical device is delivered to the target site through catheter 800, if the medical device is to remain implanted within the body at the site, catheter 800 is removed out from the body and from around the medical device. FIG. 1 shows a dashed line extending along a length of sealing assembly 820 to represent a weakened section along which sealing assembly 820 may be split apart for removal from around the implanted medical device body. Splitting apart sealing assembly 820 is necessary when a proximal end of the implanted medical device will not fit through the valve/seal member of the assembly. Other sealing assemblies known in the art, for example, the Toughy-borst type, are configured to allow the operator to expand and contract the corresponding valve/seal member such that in the contracted state, the valve/seal member seals around a device inserted therethrough, and in the expanded state the valve/seal member is sufficiently opened so that a larger proximal end of the device will fit through the valve/seal member. Having the ability to alternately expand and contract the valve/seal member can alternately facilitate the movement of devices and guide wires through the valve/seal member, when expanded, and provide better sealing, when contracted, but also requires additional manipulations from the operator, which can make the catheter delivery procedure a bit more tedious. Toughy-borst type sealing assemblies may also include a tubing port connected thereto, similar to that described above, so that fluid may be injected through catheter 800 downstream of the valve member thereof.

Although the above-described valve assemblies enable catheter delivery procedures, there is still a need for improved apparatus and methods that can prevent excessive leakage/backflow and facilitate simpler catheter delivery procedures.

BRIEF DESCRIPTION OF THE DRAWINGS

The following drawings are illustrative of particular exemplary embodiments and therefore do not limit the scope of the invention. The drawings are not to scale (unless so stated) and are intended for use in conjunction with the explanations in the following detailed description. Embodiments of the present disclosure will hereinafter be described in conjunction with the appended drawings, wherein like numerals denote like elements.

FIG. 1 is a plan view of a portion of a prior art catheter delivery system.

FIG. 7A is a plan view of the proximal section of the catheter along with a syringe adapter tool and a syringe, according to some embodiments.

FIG. 7B is a perspective view of the proximal section with the syringe adapter tool and the syringe connected thereto.

FIG. 7C is a longitudinal cross-section view of the proximal section shown in FIG. 7B, according to some embodiments.

FIG. 7D is a plan view of the syringe adapter tool, according to some embodiments.

FIG. 8A is a perspective view of an alternate embodiment of a syringe adapter tool.

FIG. 8B is an enlarged perspective view of the syringe adapter tool of FIG. 8A engaged with the proximal section of the catheter.

DETAILED DESCRIPTION

The following detailed description is exemplary in nature and is not intended to limit the scope, applicability, or configuration of embodiments disclosed herein. Rather, the following description provides practical illustrations for implementing exemplary embodiments. Examples of constructions, materials, dimensions, and manufacturing processes are provided for selected elements, and all other elements employ that which is known to those of skill in the field of the disclosure. Those skilled in the art will recognize that many of the examples provided have suitable alternatives that can be utilized.

Figure 2A:
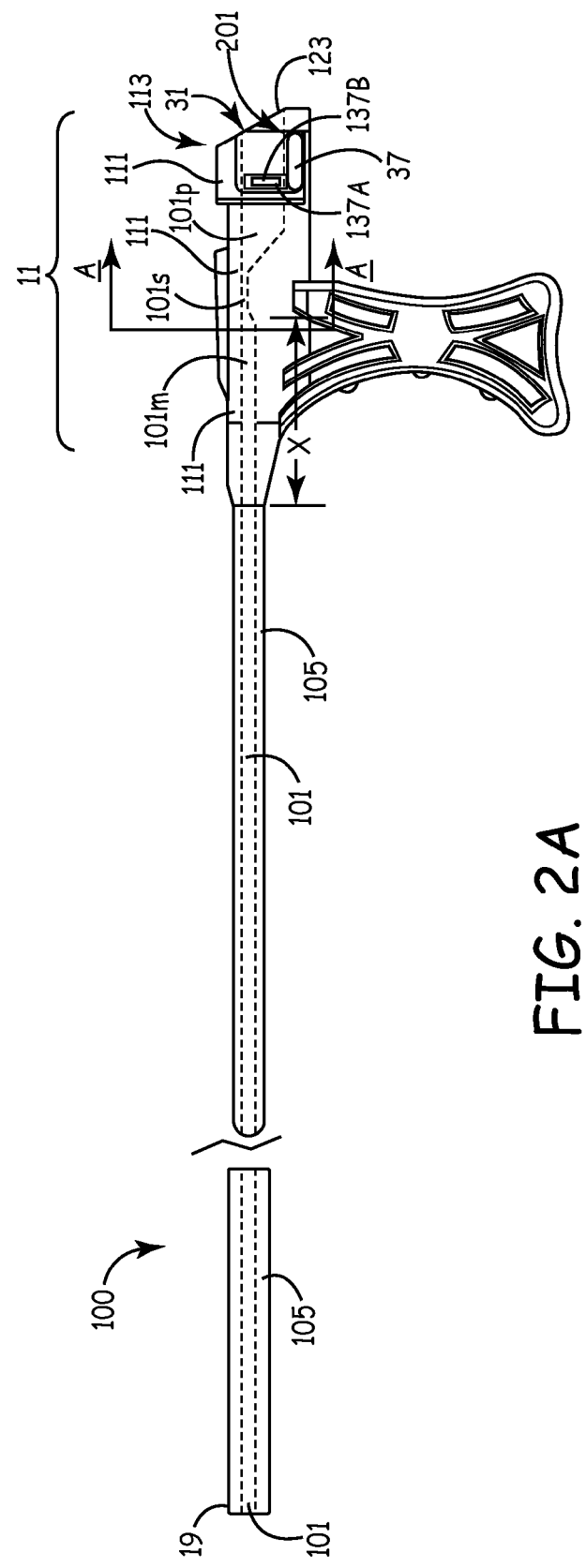
FIG. 2A is plan view of a catheter, according to some embodiments of the present invention.

FIG. 2A is plan view of a catheter 100, according to some embodiments of the present invention. FIG. 2A illustrates catheter 100 extending from a proximal section 11 thereof to a distal end 19 thereof; a lumen 101 of catheter 100 (shown with dashed lines) extends distally to distal end 19 from a proximal opening 31 thereof, which has a perimeter defined by a proximal terminal end 113 of proximal section 11. According to the illustrated embodiment, proximal terminal end 113 has a tapered profile and preferably includes an exposed sealing area 123, which is mainly exposed by virtue of the tapered profile. Exposed sealing area 123 is preferably formed from a relatively soft and resilient material, for example, a liquid silicone rubber (LSR) material or a thermoplastic elastomer (TPE) material, as compared to a material that forms a relatively rigid sidewall 111 of proximal section 11, for example, a polyether block amide such as Pebax®, which is a material commonly used in the construction of catheter sidewalls, or a polyolefin such as Pro-fax. It should be noted that, although preferred, some alternate embodiments of proximal section 11 need not include the tapered profile at proximal terminal end 113, or exposed sealing area 123.

FIG. 2A further illustrates lumen 101 including a main portion 101$m$, a seal zone portion 101$s$ and a proximal port portion 101$p$, wherein seal zone portion 101$s$ forms a passageway (i.e. having a diameter) that is smaller in size than that of each of main portion 101$m$ and proximal opening 31, in order to provide a sealing interface with an elongate body of a medical instrument/device that is passed through lumen 101. Main portion 101$m$ is shown extending distally from seal zone portion 101$s$ toward distal end 19 of catheter 100; and proximal port portion 101$p$ is shown extending distally from proximal opening 31 to seal zone portion 101$s$. Proximal port portion 101$p$ is preferably sized to receive a standard tapered tip of a syringe, for example, having a luer taper known to those skilled in the art, either in a luer-lock configuration (syringe 810, FIG. 1, and syringe 710, FIG. 7A) or in a luer slip fit configuration (syringe 210, FIG. 2C). Thus, according to an exemplary embodiment, a size of proximal opening 31 and proximal port portion 101$p$ in proximity to proximal opening 31 will accommodate insertion therein of a syringe tip having a maximum diameter of up to approximately 0.16 inch. Seal zone portion 101$s$ is preferably formed from a relatively soft and resilient material, for example, an LSR or TPE, that will elastically stretch and compress in order to provide an interference fit for sealing around larger diameter instruments/devices. According to some embodiments, which will be described in greater detail below, a relatively soft part of proximal section 11 forms both seal zone portion 101$s$ and exposed sealing area 123 and extends therebetween to define a portion of a perimeter of proximal port portion 101$p$.

An initial diameter of seal zone portion 101$s$ may be required to expand as little as approximately 1% and up to approximately 1000% in order to accommodate passage therethrough of a variety of instruments/devices that range in outer diameter from approximately 0.010 inch to approximately 0.12 inch. Some LSR and TPE materials are known to exhibit such a range of elongation, for example, Shin-Etsu KE-2090-10 LSR (980%) and Dynalloy™ OBC 8000-T05 (1800%), but a material selection for seal zone portion 101s could be rather limited by this requirement. If seal zone portion 101s is sized to particularly accommodate passage of instruments/devices that have relatively large outer diameters, for example, medical electrical leads that have diameters ranging from approximately 0.04 inch to approximately 0.09 inch, seal zone portion 101s may have a diameter that is too large to adequately seal around a smaller device/instrument, such as relatively smaller diameter guide wire 200, which may have an outer diameter of approximately 0.01 inch, or relatively larger diameter guide wire 200', which may have an outer diameter of approximately 0.03 inch; or, if seal zone portion 101s is sized to particularly accommodate passage of the relatively smaller instruments/devices, like aforementioned wires 200/200', then, unless the material of seal zone portion 101s has the necessary elongation properties, insertion of a device/instrument therethrough that is significantly larger may cause permanent deformation (i.e. plastic deformation or tearing) to seal zone portion 101s. Thus, according to some preferred embodiments of the present invention, in which seal zone portion 101s has a diameter tailored to accommodate the relatively large diameter instruments/devices, exposed sealing area 123 is useful to prevent excessive leakage/backflow from catheter 100, for example, as will be described in conjunction with FIGS. 2B-C. However, according to other preferred embodiments, in order to accommodate a larger range of diameters, seal zone portion 101s includes a slit segment 502 that extends proximally from a distal end of seal zone portion 101s and into a bore 515 of seal portion 101s, for example, as illustrated in FIG. 5A and described in greater detail below, in conjunction with FIGS. 4A-B and 5A-C.

Figure 2B:
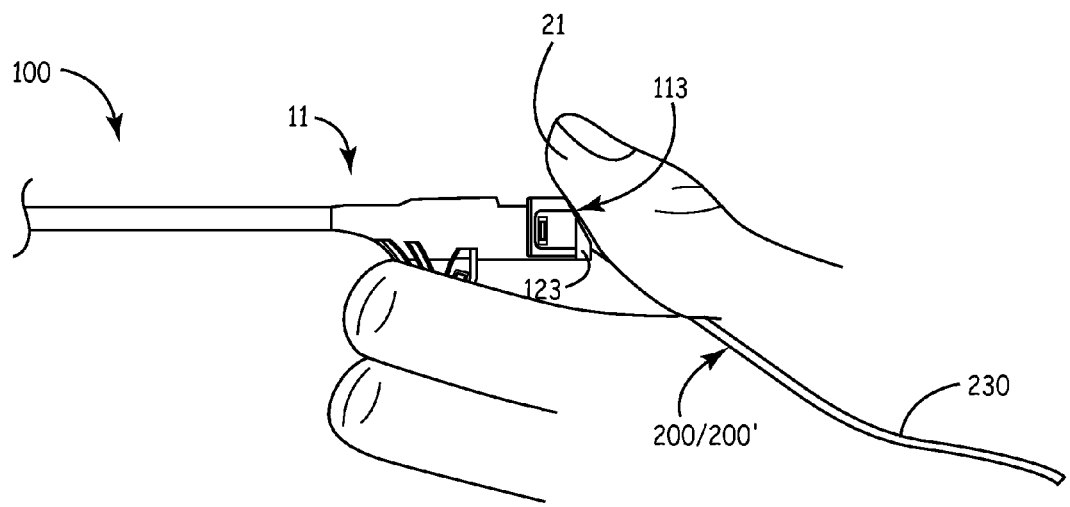
FIGS. 2B-C are schematics depicting some methods facilitated by a proximal section of the catheter shown in FIG. 2A.

FIG. 2B is a schematic depicting an operator holding proximal section 11 of catheter 100. FIG. 2B illustrates guide wire 200/200' extending proximally out from proximal terminal end 113, and a thumb 21 of the operator being held over proximal opening 31 (FIG. 2A) and pressing guide wire 200/200' against exposed sealing area 123. Guide wire 200/200' is a steerable instrument, known to those skilled in the art, which is useful for maneuvering within, for example, a venous anatomy of a patient's body. Relatively large diameter guide wire 200' may be used to introduce catheter 100 into the patient's venous system, according to methods known in the art. Once catheter 100 has been advanced over guide wire 200', so that distal end 19 (FIG. 2A) is positioned within the venous system, guide wire 200' may be exchanged for relatively small diameter guide wire 200, whose distal end 209, may be maneuvered out from distal end 19 of catheter 100 and into proximity with a target site. A therapy-delivering medical device, for example, a medical electrical lead, may then be advanced through catheter 100 and over guide wire 200 to the target site. Alternately, another type of instrument, such as a steerable electrophysiology (EP) catheter and/or a sub-selecting catheter, both known in the art, may be exchanged for large diameter guide wire 200' in order to provide access in closer proximity to the target site, prior to advancing the therapy-delivering medical device through catheter 100. In any case, while guide wire 200/200', or another comparably sized instrument, extends within catheter 100, if seal zone portion 101s is one that is tailored to seal best around larger diameter instruments/devices, for example, medical electrical leads, the operator can hold his thumb 21 over proximal opening 31 to prevent leakage of blood, and/or other fluids, from catheter 100 while the other hand of the operator (not shown) may grasp a proximal portion 230 of guide wire 200/200' to maneuver guide wire 200/200' and catheter 100 relative to one another. With reference to FIG. 2B, it may be appreciated that the tapered profile of proximal terminal end 113 orients proximal opening 31 toward thumb 21 of the operator's hand that grasps proximal section 11 of catheter 100 so that the hand may be in a more comfortable position. Furthermore, according to preferred embodiments, exposed sealing area 123 provides a relatively smooth transition and strain relief for that portion of guide wire 200 extending from proximal terminal end 113, when thumb 21 is held as shown. Exposed sealing area 123 may also have a relatively lubricious surface, so that the operator may push and pull guide wire 200 between thumb 21 and area 123 with relative ease.

Figure 2C:
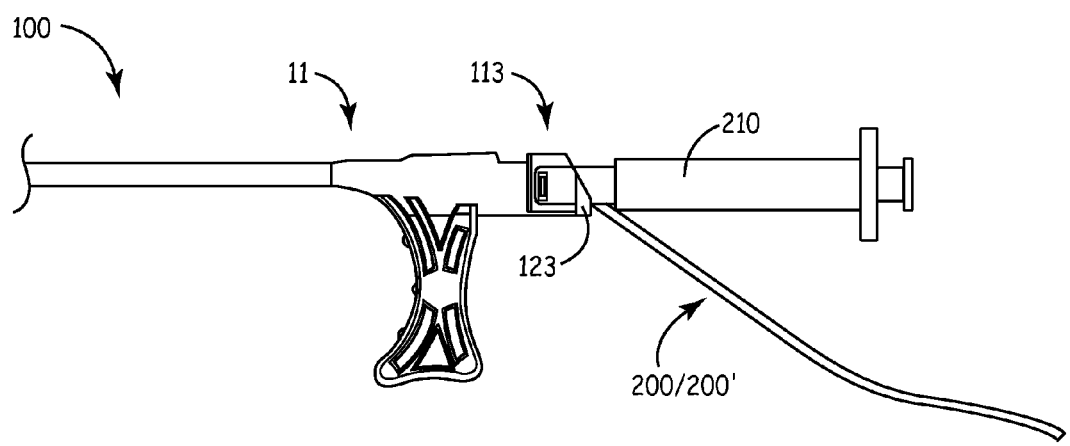

FIG. 2C is a schematic depicting a standard tapered tip (slip-tip configuration) of a syringe 210 inserted into proximal section 11 of catheter 100 through proximal opening 31 (FIG. 2A) alongside guide wire 200/200', so, like in FIG. 2B, guide wire 200/200' is pressed against exposed sealing area 123. The fit of the tip of syringe 210 alongside guide wire 200/200', within proximal opening 31, preferably seals against backflow/leakage while syringe 210 is used to inject fluid into catheter lumen 101, for example, a saline flush or a radiopaque contrast agent that is useful to visualize anatomy in which catheter 100 and guide wire 200/200' are being maneuvered, as was described above. According to the illustrated embodiment, when syringe 210 is filled with the contrast agent, the operator may inject a series of small volumes of the agent, or 'puffs', while maneuvering guide wire 200/200' and/or catheter 100. Furthermore, as described above, exposed sealing area 123 preferably provides a smooth transition and strain relief for guide wire 200/200' and may have a relatively lubricious surface to allow the operator to move guide wire 200/200' between the tip of syringe 210 and exposed sealing area 123, without significantly compromising the sealing interface therebetween.

With reference back to FIG. 2A, a relatively soft inner surface 201 preferably defines a portion of a perimeter of proximal port portion 101p of lumen 101, just inside proximal opening 31 and extending distally therefrom; inner surface 201 may be an integral extension of exposed sealing area 123, as mentioned above and further described below. Relatively soft inner surface 201 may provide additional sealing and strain relief at the interface between guide wire 200/200' and the inserted tip of syringe 210. It should be noted that some operators may prefer to maneuver catheter 100 without any guide wire extending therein, in which case, the fit of syringe 210 within proximal opening 31, without any guide wire extending therethrough, and with or without relatively soft inner surface 201, also seals against backflow/leakage.

With reference back to the prior art system of FIG. 1, it may be appreciated that syringe 810 coupled to side tubing port 826 of sealing assembly 820, via stopcock 827, is a relatively bulky set up compared to the inline attachment of syringe 210 with proximal section 11 of catheter 100, according to the assembly illustrated in FIG. 2C, and that this inline attachment can make the maneuvering of catheter 100, either with or without guide wire 200/200' extending therein, less cumbersome. According to some embodiments of the present invention, which will be described below, in conjunction with FIGS. 7A-D and 8A-B, a syringe adapter tool may be provided to further facilitate the inline attachment of a syringe.

Figure 3A:
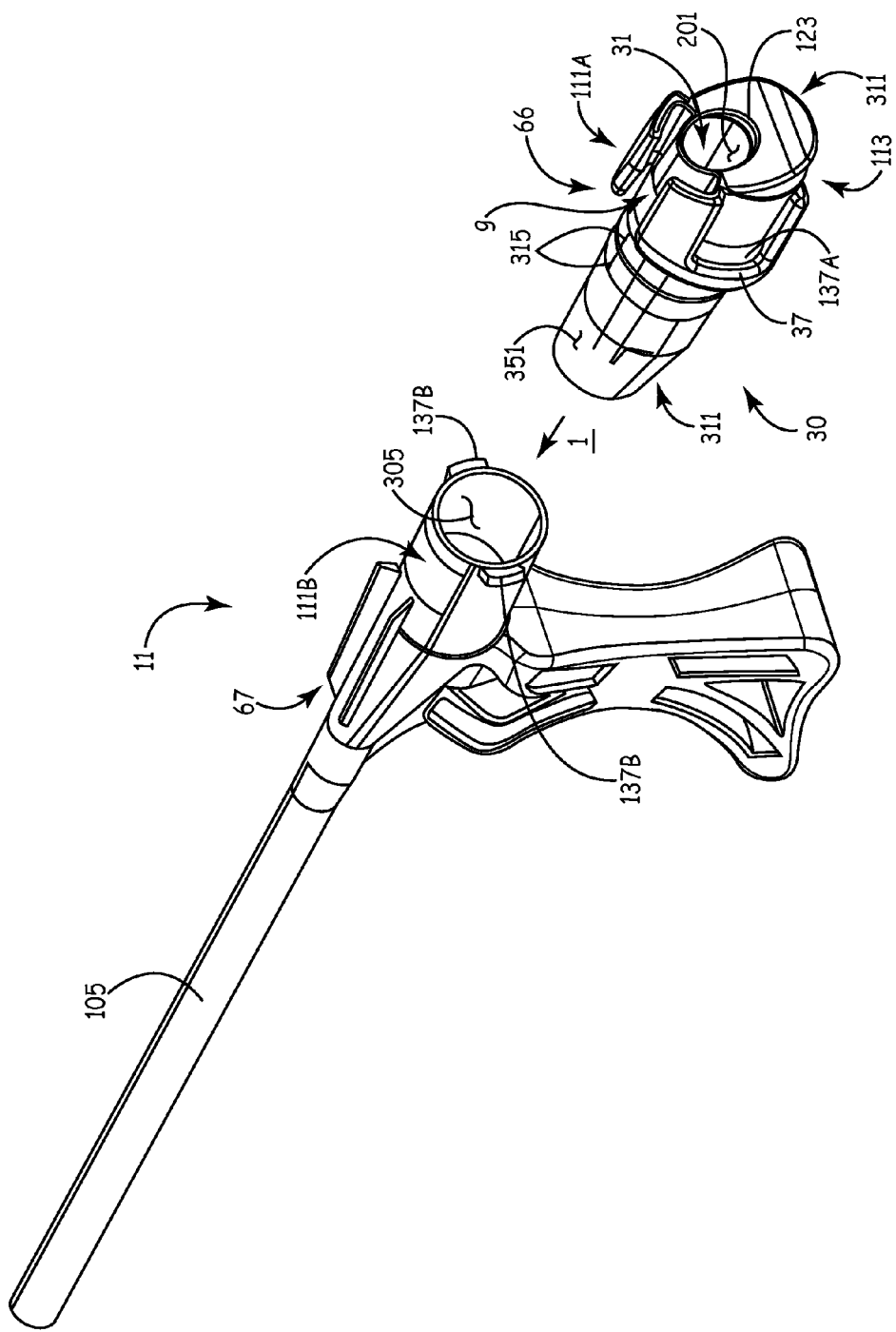
FIG. 3A is an exploded perspective view of the proximal section of the catheter of FIG. 2A, according to some embodiments of the present invention.
Figure 3B:
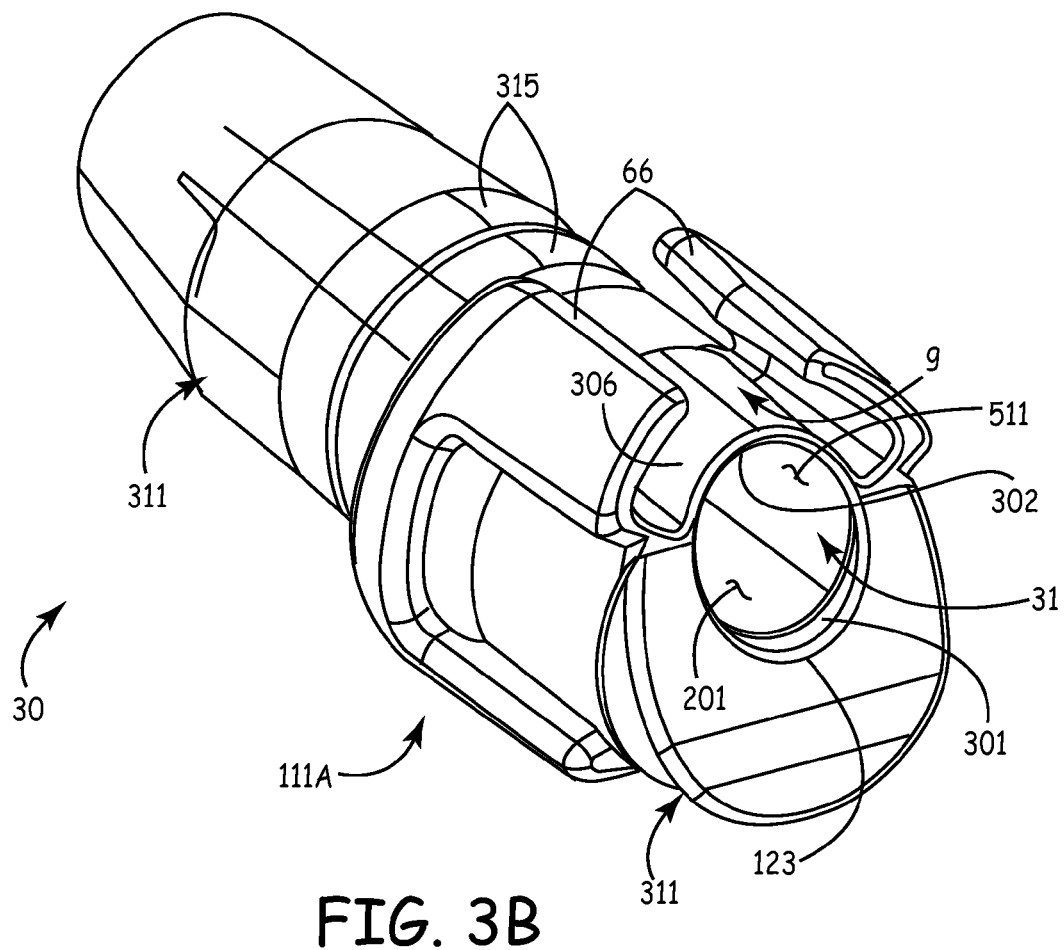
FIG. 3B is a perspective view of a sealing assembly, according to some embodiments.

FIG. 3A is an exploded perspective view of proximal section 11 of catheter 100, according to some embodiments of the present invention. FIG. 3A illustrates relatively rigid sidewall 111 of proximal section 11 including two relatively rigid separable parts 111A, 111B, and further illustrates exposed sealing area 123 being formed by a relatively soft part 311 that is fixedly attached to part 111A of the two separable parts to form a sealing assembly 30, another perspective view of which is shown in FIG. 3B. Relatively soft part 311 has a lower durometer than parts 111A, 111B, which lower durometer may be within the range of 0 to 60 on a Shore A scale, or even lower, for example, on the Shore OO scale. It should be noted that the terms 'soft' and 'hard' ('hard' with respect to surfaces of the relatively rigid parts described herein) are used throughout to indicate relative durometers. FIG. 3A further illustrates part 111B of the two relatively rigid separable parts being in the form of a hub which is coupled to a tubular member 105 of catheter 100. With reference back to FIG. 2A, tubular member 105 is shown extending from proximal section 11 to distal end 19 of catheter 100, according to some embodiments.

Figure 3C:
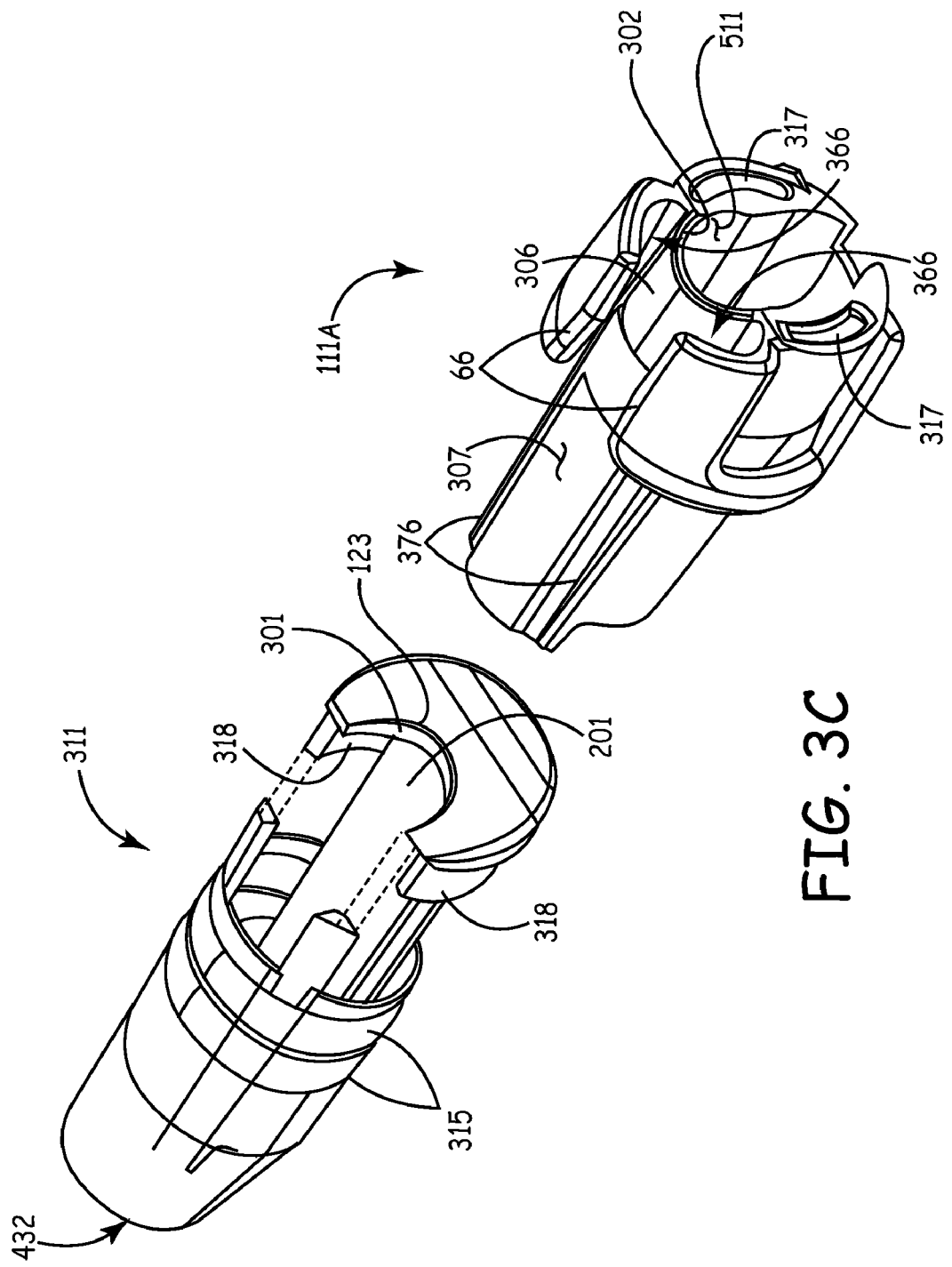
FIG. 3C is an exploded perspective view of the sealing assembly, according to some embodiments.

According to the illustrated embodiment, sealing assembly 30 may be formed independently of the remainder of catheter 100, for example, by a two shot molding process known in the art, wherein a first shot forms relatively rigid part 111A and a second shot forms relatively soft part 311 within and around part 111A. FIG. 3C is an exploded perspective view of sealing assembly 30, according to some embodiments, in which relatively rigid part 111A and relatively soft part 311 are separated from one another. According to some preferred embodiments, an adhesion of soft part 311 to rigid part 111A, as well as some mechanical interlocking therebetween, fixedly attaches soft part 311 to rigid part 111A. For example, FIG. 3C illustrates female features 317 formed in relatively rigid part 111A for interlocking with male features 318 of relatively soft part 311, according to some embodiments. To further secure/attach soft part 311 to rigid part 111A, soft part 311 may also be formed with optional bridges, or belts, for example, indicated with dashed lines in FIG. 3C and by reference numeral 31b in FIGS. 4A and 5A. The material forming relatively rigid part 111A may be Pebax® or any other suitable relatively rigid and biocompatible material known in the art, such as a polyolefin, and the material forming relatively soft part 311 may be LSR or TPE. According to a first exemplary embodiment, a material forming relatively rigid part 111A is Pebax® 7033 (available from Arkema), and a material forming relatively soft part 311 is CLS2000 LSR (available from Momentive); according to a second exemplary embodiment, a material forming relatively rigid part 111A is 6523 Pro-fax polypropylene (available from LyondellBasell Industries), and a material forming relatively soft part 311 is either Dynaflex™ G-6703 TPE (available from GLS Corporation), or Medalist® MD-100 TPE (available from Teknor Apex).

FIG. 3B further illustrates the perimeter of proximal opening 31 including a first portion 301 and a second portion 302, according to some preferred embodiments, wherein first portion 301 protrudes proximally from second portion 302, by virtue of the tapered profile of proximal terminal end 113, and exposed sealing area 123, which forms first portion 301, is exposed by virtue of first portion 301 protruding proximally from second portion 302. With further reference to FIG. 3C, it may be appreciated that, according to the illustrated embodiment, a single bulk of material, that is relatively soft part 311 (second shot), forms exposed sealing area 123, relatively soft inner surface 201 of proximal port portion 101p of lumen 101 and seal zone portion 101s of lumen 101. Alternatively, separate bulks of material may employed, for example, a first bulk for exposed sealing area 123 and soft inner surface 201, and a second bulk for seal zone portion 101s, being segregated from one another along the dashed line shown in FIG. 5A. According to these alternate embodiments, the two materials may be the same or different, each preferably either an LSR or a TPE, for example, as described above.

Sealing assembly 30 may be connected to hub/relatively rigid second part 111B of catheter 100 by insertion therein, per arrow I of FIG. 3A. FIGS. 3A-C further illustrate external sealing ridges 315 formed in relatively soft part 311 of assembly 30 and supported by an underlying wall 307 of relatively rigid part 111A; sealing ridges 315 are located along assembly 30 in order to sealingly engage with an inner surface 305 of hub 111B when connected thereto. The fit of this sealing interface between ridges 315 and inner surface 305 may be sufficient to secure assembly 30 to proximal section 11, however, according to some preferred embodiments, relatively rigid part 111A of assembly 30 includes at least one aperture 137A within which a corresponding protruding nub 137B of hub 111B engages to further secure the connection of assembly 30. FIG. 2A shows nub 137B engaged within aperture 137A, and, with reference to FIGS. 2A and 3A, sealing assembly 30, after being secured to hub 111B, may be removable therefrom, for example, by lifting a segment 37, which surrounds aperture 137A, of relatively rigid part 111A from around nub 137B and pulling back on assembly 30, in a direction opposite to arrow I.

Figure 4A:
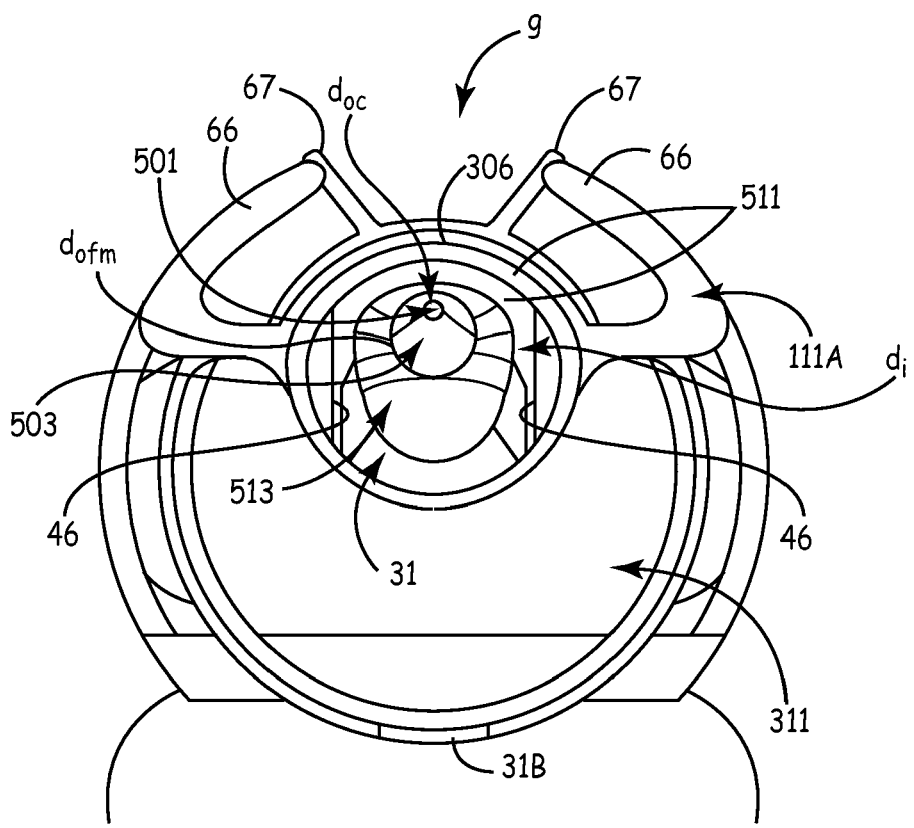
FIGS. 4A-B are end views of the sealing assembly within the catheter of FIG. 2A, according to some embodiments.
Figure 4B:
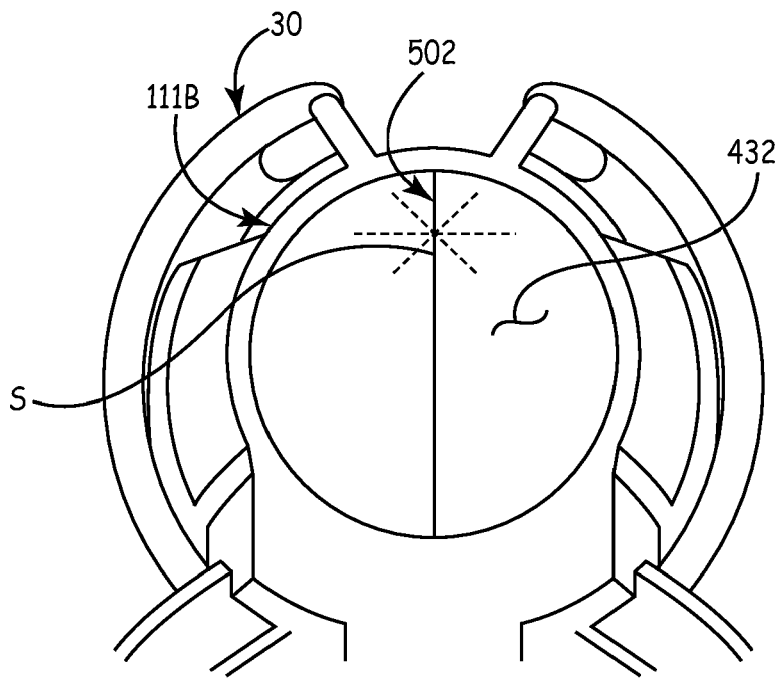
Figure 5A:
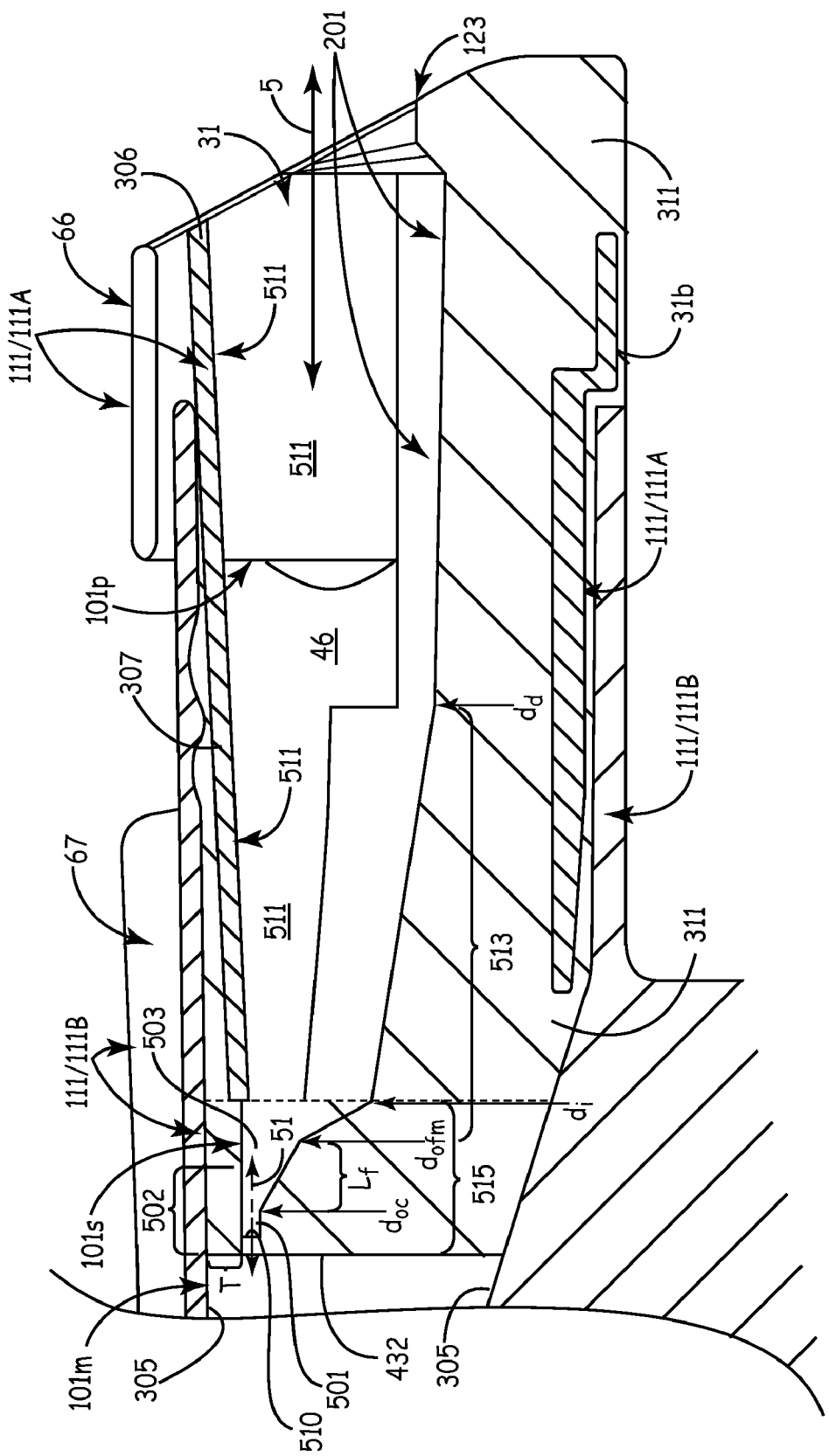
FIG. 5A is a longitudinal cross-section view through the sealing assembly within the catheter of FIG. 2A, according to some embodiments.

FIG. 4A is an end view of catheter 100, looking into lumen 101 (FIG. 2A) at proximal opening 31, and FIG. 4B is a cross-section view through section line A-A of FIG. 2A, in order to show opposite ends of relatively soft part 311 of sealing assembly 30, according to some embodiments; and FIG. 5A is a longitudinal cross-section view through sealing assembly 30 within catheter 100, according to some preferred embodiments. With reference to FIGS. 4A-B and 5A, bore 515 in combination with slit segment 502, which is defined by a slit S, make up seal zone portion 101s of lumen 101. According to the illustrated embodiment, bore 515 includes cylindrical segment 501 and funnel-like segment 503; and a distal terminal end 510 of bore 515 is proximally offset from a distal face 432 of relatively soft part 311. With reference to FIGS. 4B and 5A, slit S, that defines slit segment 502, can be seen formed in distal face 432 and extending longitudinally along a depth from distal face 432 in order to intersect with and extend through funnel-like segment 503. (One or more additional slits, for example, along the dashed lines in FIG. 4B, may further define slit segment 502, according to alternate embodiments.) It should be noted that cylindrical segment 501, according to some alternate embodiments, is not included in bore 515, so that bore only includes funnel-like segment 503, which terminates at distal terminal end 510. Furthermore, with reference to FIGS. 4A and 5A, it may be appreciated that the tapering aspect of segment 503 is asymmetrical about a central longitudinal axis 510 of seal zone portion 101s, or confined to only a portion of a perimeter of segment 503 rather than encompassing an entire perimeter thereof, thus the term 'funnel-like' is used to distinguish from a symmetrical conical shape typically associated with the term 'funnel'. However, it should be noted that, according to some alternate embodiments, funnel-like segment 503 may have a symmetrical conical shape.

An unexpanded diameter $d_{oc}$ of cylindrical segment 501 may be approximately 0.01 inch, for example, to seal around devices instruments having an outer diameter of approximately 0.012 inch and larger, and a maximum, proximal unexpanded diameter $d_{ofm}$ of funnel-like segment 503 may be approximately 0.05 inch, for example to seal around devices/instruments having an outer diameter of approximately 0.045 to 0.055 inch and larger. According to some exemplary embodiments, distal terminal end 510 of bore 515 is offset, proximally, from distal face 432 by a distance of approximately 0.015 inch; an overall length of cylindrical segment 501 is between approximately 0.01 inch and approximately 0.02 inch; an overall length $L_f$ of funnel-like segment 503 is approximately 0.05 inch; and slit segment 502 extends proximally, into funnel-like segment 503, over a length of approximately 0.025 inch. It should be noted that, according to some alternate embodiments, overall length $L_f$ of funnel-like segment 503 can be long enough to reach proximally, closer to proximal opening 31.

Figure 5B:
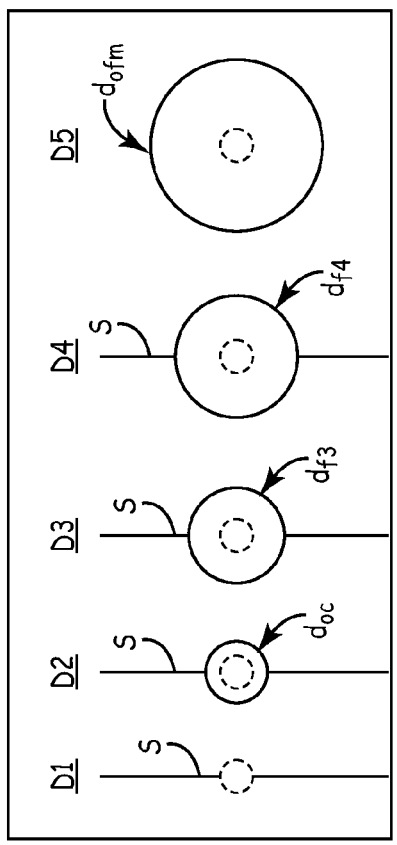
FIGS. 5B-C are schematic series of radial sections at various depths along a seal zone portion of a lumen of the sealing assembly of FIGS. 4A-B and 5A.
Figure 5C:
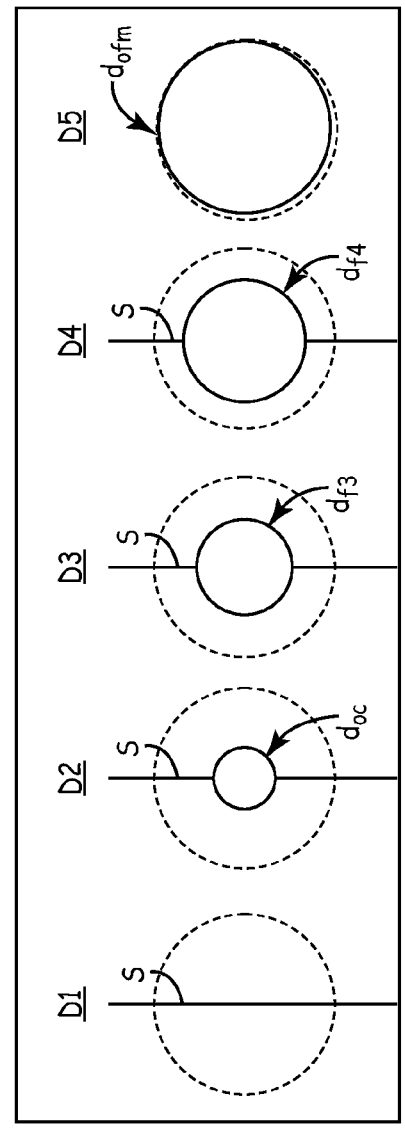
Figure 5D:
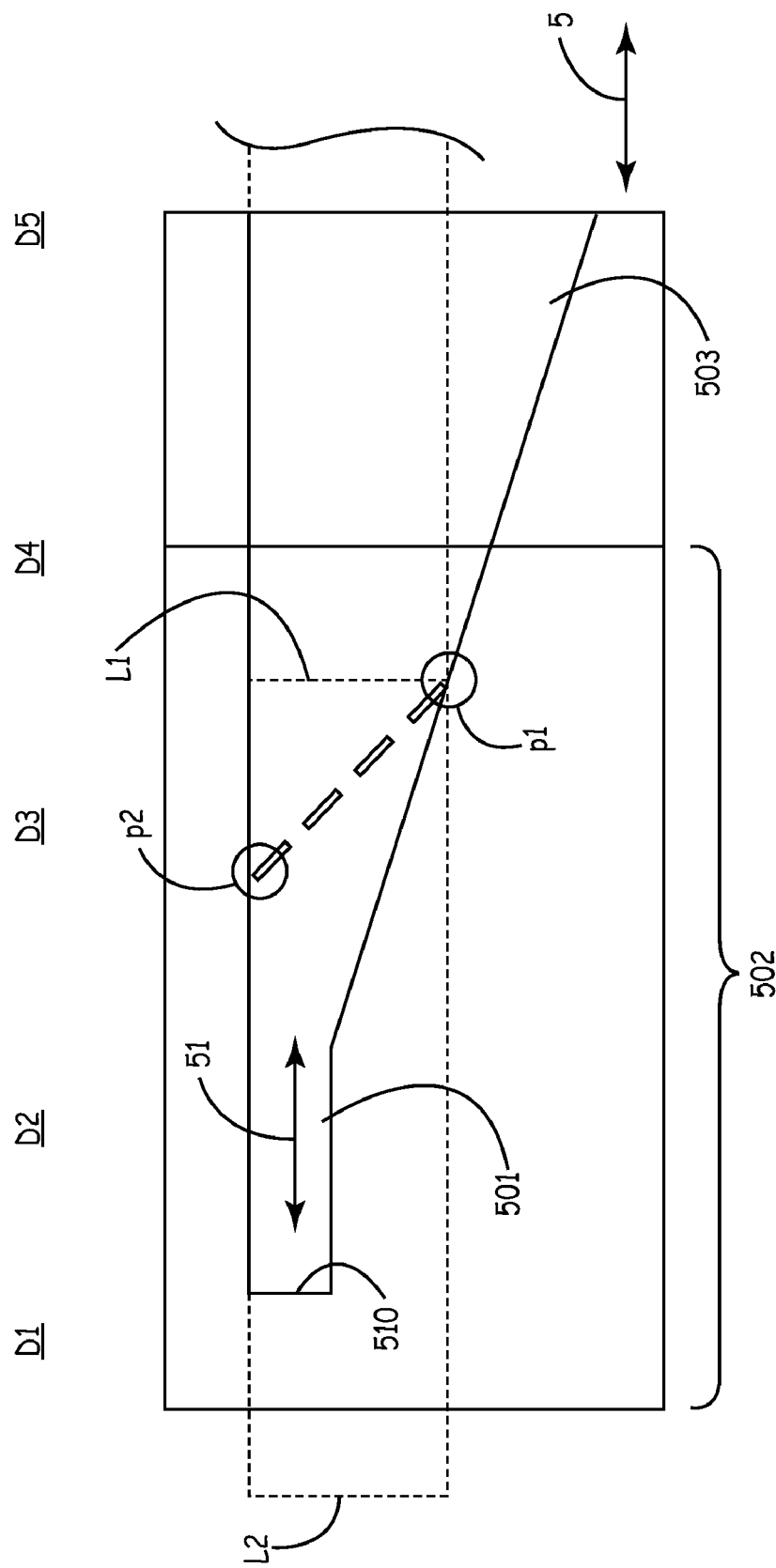
FIG. 5D is a schematic side view along the seal zone portion of the lumen, according to some embodiments.

The longitudinal extent of slit segment 502, between distal face 432 and distal terminal end 510 of bore 515, can act like a one-way valve to enhance the sealing function of seal zone portion 101s, particularly when no instrument/device is passed through seal zone portion 101s or when a relatively small diameter instrument/device (smaller than cylindrical segment diameter $d_{oc}$), for example, guide wire 200/200', is passed through seal zone portion 101s; while the extent of slit segment 502 into funnel-like segment 503 provides additional capacity for segments 501, 503 to expand, for example, without plastic deformation or tearing, and thereby accommodate passage of larger diameter devices/instruments, for example, up to approximately 0.12 inch diameter, into and/or through seal zone portion 101s. When catheter 100 is inserted within a patient's body, for example, venous system, and when no instrument/device, or a relatively small diameter instrument/device, is inserted through seal zone portion 101s, a back-pressure within main portion 101m of catheter lumen 101 exerts a force against distal face 432 to cause confronting faces of slit S, in proximity to distal face 432, to seal together and thereby prevent all, or most of backflow out through proximal opening 31. A depth of slit segment 502 in conjunction with a durometer and elongation and compression properties of the bulk of material, i.e. soft part 311, and an interference fit of soft part 311 within sidewall 111 of catheter 100, along the depth of slit segment 502, which provides for some compressive pre-loading of slit segment 502, are all interrelated factors contributing to this sealing integrity. When a relatively large diameter instrument/device is inserted through seal zone portion 101s, the longitudinal extent of slit segment 502 into funnel-like segment 503 facilitates expansion of the smaller diameter portions of funnel-like segment 503, through which slit segment 502 extends, and of cylindrical segment 501, around a larger instrument/device inserted therethrough, while the larger diameter portion of funnel-like segment 503, which is located proximal to a proximal termination of slit segment 502 and which is smaller than the diameter of the larger diameter instrument/device, seals around a perimeter of the larger diameter instrument/device. Furthermore, funnel-like segment 503 can decrease the force necessary to push a relatively larger instrument/device into the smaller diameter portions of seal zone portion 101s. FIGS. 5B-D schematically illustrate various diameter instrument/devices in relation to seal zone portion 101s, according to some embodiments, and will be described below.

Seal zone portion 101s of lumen 101 is preferably integral within the single bulk of material that is relatively soft part 311 of sealing assembly 30, for example, as shown in FIG. 3C, and, according to some preferred embodiments, an entirety of bore 515 and slit segment 502, which define seal zone portion 101s, are formed in this bulk of material, along with relatively soft inner surface 201 of proximal port portion 101p and exposed sealing area 123. The dashed line of FIG. 5A designates a proximal termination, or opening of bore 515, and, as pointed out, above, in conjunction with FIG. 3C, can also indicate a dividing line between two separate bulks of material, according to some alternate embodiments, wherein seal zone portion 101s is formed in the distalmost of the two separate bulks. In either case, it should be noted that the incorporation of seal zone portion 101s within hub/relatively rigid part 111B of catheter 100 and in relatively close proximity to the junction of tubular member 105 with hub 111B, makes proximal section 11 of catheter 100 more compact, lengthwise, than many prior art systems, such as that illustrated in FIG. 1, in which separate seal/valve assembly 820 can add some significant length to catheter 800. With reference back to FIG. 2A the proximity of seal zone portion 101s to the proximal junction of tubular member 105 is indicated by a distance X, which may be between approximately 0.25 and 0.5 inch, according to some embodiments. A profile of catheter in proximity to the proximal junction of tubular member 105 typically increases and thereby limits a depth of the insertion of catheter 100 into a patient's body; thus, an advantage of this more compact length, i.e. distance X, is in allowing for more of a length of an instrument/device, such as a medical electrical lead, within catheter 100, to extend into the patient's body and reach a more distal target site. It should be noted that a seal member formed according to any of the embodiments of seal zone portion 101s, which are described herein, although described for inclusion in a proximal portion of a catheter, may alternately be incorporated in other types of medical devices/instruments, and, furthermore within a distal portion of various types of medical instruments/devices, according to some embodiments.

Each of FIGS. 5B-C is a schematic series of radial sections at various depths, D1-D5, along seal zone portion 101s, according to the embodiments described above (FIGS. 4A-B and 5A). The dashed outline of FIG. 5B represents a perimeter of a relatively small diameter device/instrument, while the dashed outline of FIG. 5C represents a perimeter of a relatively large diameter device/instrument. Depth D5 is at a location coinciding with maximum, unexpanded diameter $d_{ofm}$ of funnel-like segment 503; depths D4 and D3 are at locations within an extent of funnel-like segment 503; depth D2 is at a location within an extent of cylindrical segment 501, or at a third location within funnel-like segment 503, if no cylindrical segment is included; and depth D1 is at a location between distal face 432 and the distal terminal end 510 of bore 515. Although, in neither of the FIGS. 5B-C, slit S is shown expanded, it should be understood that, in FIG. 5B, slit S opens at depth D1 to accommodate the illustrated perimeter of the relatively small diameter device/instrument, and, in FIG. 5C, slit S opens at each of depths D1-D4 to accommodate the illustrated perimeter of the relatively large diameter device.

According to FIG. 5B, sealing takes place at, and around depth D1, between distal face 432 and the distal end of cylindrical segment 501, and is accomplished by the above-described back-pressure that forces confronting faces of slit S together around the perimeter of the device/instrument. In the absence of back-pressure, or with relatively low back-pressure, relatively rigid sidewall 111 (FIG. 5A) provides sufficient compressive pre-loading to the bulk of material forming relatively soft part 311 around seal zone portion 101s to help to hold the confronting faces of slit S together for sealing. With reference again to FIGS. 4A-B, the orientation of slit S, on a plane that symmetrically divides part 311, along sealing zone portion 101s, facilitates preferential pre-loading of the confronting faces of slit S toward one another. Furthermore, with reference to FIGS. 3A-B and 5A, an outer surface 351 of soft part 311 that corresponds with seal zone portion 101s is preferably sized for an interference fit within inner surface 305 of relatively rigid second part/hub 111B, in proximity to the junction with tubular member 105, where inner surface 305 tapers down, as best seen in FIG. 5A. The interference fit may be uniform about a circumference of part 311 along seal zone portion 101s, or one or both of inner surface 305 and outer surface 351 may have a profile to make compressive pre-loading greater in the direction of the confronting faces of slit S. According to an exemplary embodiment, the interference fit is approximately 10% of an outer diameter of part 311, when the material forming part is one of the aforementioned CLS2000 LSR, Dynaflex™ G-6703 TPE, and Medalist® MD-100 TPE. Although FIG. 5A shows inner surface 305 of second part/hub 111B is tapering inward, toward lumen main portion 101m, along a length of the aforementioned interference fit with part 311, in alternate embodiments, inner surface 305 does not taper along this length.

According to FIG. 5C, it may be appreciated that, at depths D1-D3, the spreading apart of slit S, to allow passage of the relatively large diameter instrument/device, can result in a gap that could allow for some leakage between the perimeter of the instrument/device and the faces of slit S. However, as the diameter of the funnel-like segment 503 increases, from diameter $d_{f3}$ (D3) to diameter $d_{f4}$ (D4), and from diameter $d_{f4}$ to diameter $d_{ofm}$ (D5), the gap decreases (D3 to D4) and disappears (D4 to D5) for a more tightly conforming seal interface around the perimeter of the larger diameter device/instrument. For example, if depth D4 corresponds to a distal termination of slit S and diameter $d_{f4}$ is approximately equal to 0.03 inch and diameter $d_{ofm}$ has a diameter approximately equal to 0.05 inch, the perimeter of funnel-like segment 503, over the length between D4 and D5, will expand as little as approximately 10% and up to approximately 83% in order to accommodate passage therethrough of a medical electrical lead having a diameter of approximately 0.055 inch.

FIG. 5D is a schematic side view of seal zone portion 101s, according to some embodiments, for example, as described above (FIGS. 4A-B and 5A). Dashed lines in FIG. 5D indicate an instrument/device, which has a mid-sized diameter (i.e. between the above-described relatively small and relatively large diameters), at two positions with respect to slit segment 502 of the seal zone portion, wherein the two positions are identified by L1 and L2 at the leading distal end of the instrument/device. With reference to the first position L1, at which the leading end is inserted into slit segment 502, just past depth D4 at the proximal terminal end of slit segment 502 (indicated with a dotted line), it may be appreciated that, due to the tapering of funnel-like segment 503, both proximal to, and within slit segment 502, a force required to push the instrument/device through the seal zone portion is lower than if the leading end of the instrument/device were to directly address slit segment 502 and a relatively small diameter bore, for example, corresponding to cylindrical segment 501. Furthermore, due to the asymmetry of funnel-like segment 503 and the above-described radial offset of central longitudinal axis 51 from central longitudinal axis 5, as the instrument/device enters slit segment 502, within funnel-like segment 503, and the leading end approaches position L2, the instrument/device preferentially opens up one side of the slit segment 502 such that the double dashed line, from point p1 to point p2, indicates the proximal-most line of a conforming/"sealing" interface between the inner surface of funnel-like segment 503 and the perimeter of the instrument/device. However, it should be noted that, according to alternate embodiments, wherein segment 503 is formed as a symmetrical funnel, the proximal-most line of the conforming interface corresponds to a radial section in proximity to point p1 of FIG. 5D.

With reference back to FIG. 5A, a transition zone 513 extends from proximal port portion 101p to seal zone portion 101s, in order to help guide insertion of a relatively large instrument/device, for example, having a diameter in the range from approximately 0.04 inch to approximately 0.12 inch (i.e. a medical electrical lead, an EP catheter or a sub-selecting catheter), from proximal port portion 101p into seal zone portion 101s of lumen 101, without the need for any special tool, for example, like the prior art tool 822, described in conjunction with FIG. 1. According to the illustrated embodiment, at least a portion of a perimeter of transition zone 513 tapers down along a first slope, distally from a point $d_d$ of proximal port portion 101p, and then tapers further distally, along a second, steeper slope, down to maximum diameter $d_{ofm}$ of funnel-like segment 503. According to some exemplary embodiments, a cross-sectional area of proximal port portion 101p at point $d_d$ accommodates a diameter of approximately 0.14 inch, and a cross-sectional area of transition zone 513, at a point $d_t$ accommodates a diameter of approximately 0.09 inch; a longitudinal distance between point $d_d$ and point $d_t$ is approximately 0.3 inch; and point $d_t$ is proximally is offset from maximum diameter $d_{ofm}$ of funnel-like segment 503, which is approximately 0.05 inch, by a distance of approximately 0.03 inch.

It should be noted that point $d_t$ corresponds with a proximal end of bore 515, such that a an entire perimeter of a distal section of transition zone 513, which tapers along the second slope, from point $d_t$ to diameter $d_{ofm}$, is surrounded by the relatively soft material of relatively soft part 311, while only a portion of a perimeter of a proximal section of transition zone 513, which tapers along the first slope, is surrounded by the relatively soft material, to form a distal extension of relatively soft inner surface 201, which was described above in conjunction with FIGS. 2A and 3A-B. A remainder of the perimeter, extending not only along the proximal section of transition zone 513 but along an entire length of proximal port portion 101p, opposite relatively soft inner surface 201, is defined by a relatively hard inner surface 511 of relatively rigid part 111A of sealing assembly 30. According to the illustrated embodiment, the location and extent of relatively hard inner surface 511 can facilitate removal of catheter 100 from around an implanted device body by slitting therethrough, as will be described in greater detail below.

Figure 6:
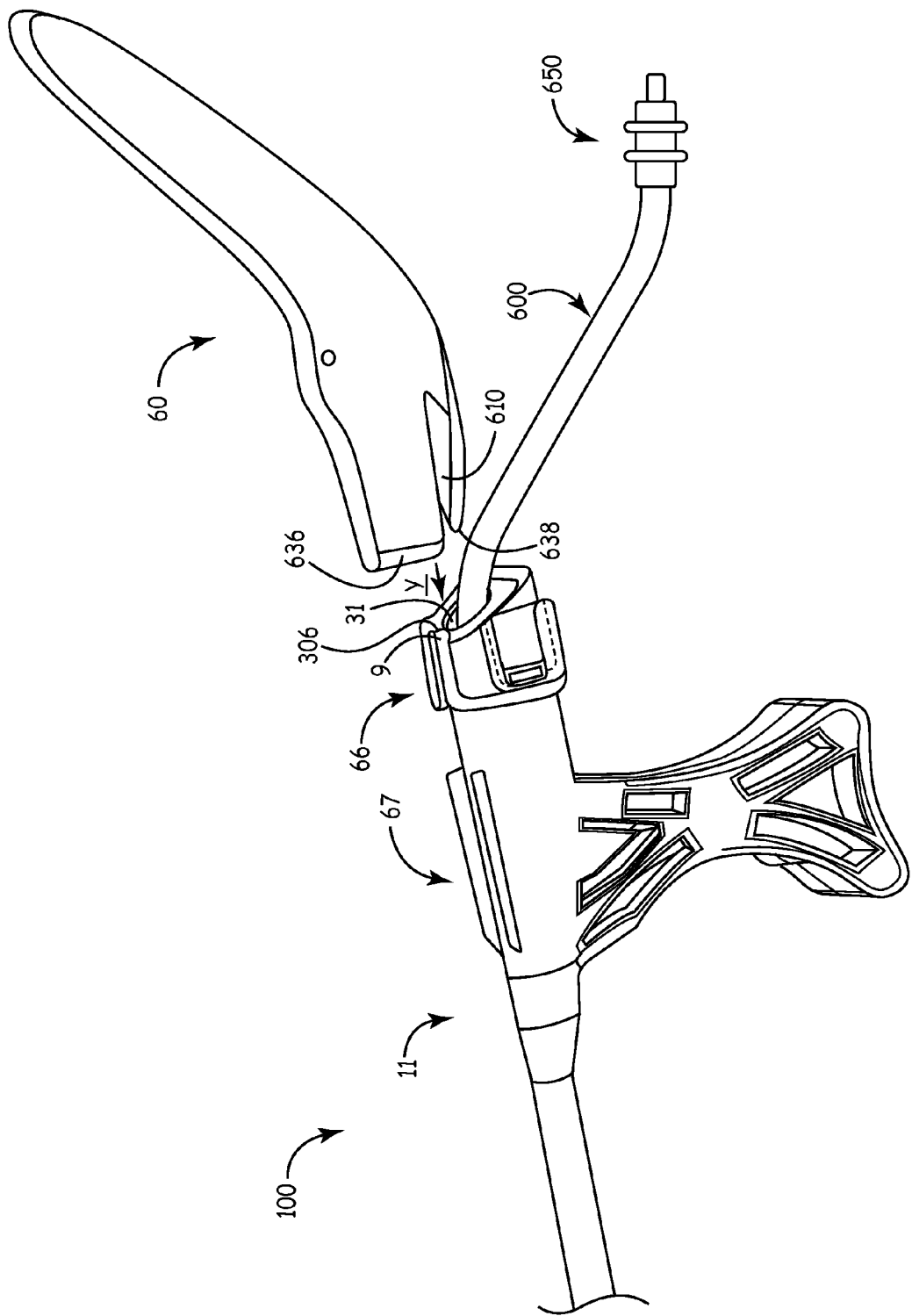
FIG. 6 is a perspective view of the proximal section of the catheter along with a slitter tool, according to some embodiments.

FIG. 5A further illustrates central longitudinal axis 51 of seal zone portion 101s being radially offset from a central longitudinal axis 5 of proximal opening 31, according to some embodiments, for example, to also facilitate removal of catheter 100 from around an implanted device body by slitting, for example, with a tool 60 that is shown in FIG. 6. However, with further reference to FIG. 5A, a minimum thickness T of relatively soft part 311 of sealing assembly 30, between seal zone portion 101s and surrounding rigid sidewall 111, is preferably no less than approximately 0.01 inch, to allow for sufficient compressive sealing about an entire perimeter of the instrument/device passed therethrough.

FIG. 6 is a perspective view of proximal section 11 of catheter 100, along with slitter tool 60, according to some embodiments, wherein tool 60 is positioned for insertion, per arrow Y, into proximal opening 31, alongside a body of an implanted medical electrical lead 600. Lead 600 is shown including a connector 650, which may be configured according to an industry standard, for example, IS-1, DF-1, IS-4 or DF-4, and may have a profile that does not allow catheter 100 to be removed thereover, for example, due to the connector and/or due to an anchoring sleeve mounted thereon, which has a profile too large to fit through catheter 100. Due to the profile of lead 600, and/or to generally facilitate the removal of catheter from around lead 600, once lead has been delivered through catheter 100 and a distal tip 690 of lead 600 (FIG. 9) is implanted at a target site in a body of a patient, slitter tool 60 is used to cut through the sidewall of catheter 100 so that it may be peeled away from around lead 600 while catheter 100 is withdrawn from the body of the patient. Those skilled in the art are familiar with slitter tools similar to tool 60 and with methods for removing catheters from around implanted lead bodies by slitting through sidewalls of catheters, so only those details of FIG. 6 that are relevant to embodiments of the present invention will be described.

FIG. 6 illustrates proximal section 11 including an external engagement feature 66 that is located in proximity to proximal opening 31, for example, being formed in relatively rigid part 111A of sealing assembly 30, which is best seen in FIG. 3B. According to the illustrated embodiment, external engagement feature 66 defines a gap g into which an operator may direct a leading edge feature 636 of tool 60 for an interlocking engagement between tool 60 and proximal section 11; when feature 636 of tool 60 engages within gap g of feature 66, lead 600 may be contained in a groove (not shown) that is formed in a lower surface of tool 60, below a nose feature 638 thereof, and a blade 610 of tool 60 comes into contact with a proximal edge of a relatively thin wall section 306 of relatively rigid sidewall 111/111A of proximal section 11, which spans gap g and may be better seen in FIGS. 3B-C and 4A. As the operator begins to slit through wall section 306, feature 636 of tool 60 is constrained within gap g by opposing sides of feature 66.

With further reference to FIG. 4A, in conjunction with FIG. 5A, it may be appreciated how the aforementioned offset of central longitudinal axis 51 of seal zone portion 101s of lumen 101 provides for a relatively thin wall section extending along a length of sealing assembly 30 in order to facilitate the continued slitting with tool 60. Thus, it may be appreciated that, in addition to providing an interlocking engagement with slitter tool 60, external engagement feature 66 of catheter proximal section 11 also serves as a visual cue for the operator to properly orient blade 610 of slitter tool 60 with the proximal edge of relatively thin wall section 306 in order to commence slitting along a path that extends through the relatively thin wall section of sealing assembly 30. As mentioned above, relatively hard inner surface 511 defines a portion of the perimeter of proximal port portion 101p, which portion generally corresponds to second portion 302 of proximal opening (FIG. 3B) and extends distally from the proximal edge of relatively thin wall section 306. An extent of relatively hard inner surface 511 maintains a 'solid' interface with nose feature 638 and, according to some preferred embodiments, for example, as illustrated in FIG. 5A, relatively hard inner surface extends all the way to point $d_i$ in order to keep blade 610 on a slitting path that intersects with slit segment 502 of seal zone portion 101s; otherwise, if blade 610 were to interface with a relatively soft inner surface, for example, anywhere along a length of proximal port portion 101p, the operator may have a more difficult time in keeping blade 610 from wandering outward, away from axis 510 before reaching seal zone portion 101s.

With reference back to FIG. 3C, some weakened areas are shown formed in relatively rigid part 111A in order to further facilitate slitting with tool 60, according to some preferred embodiments. FIG. 3C illustrates recesses 366, which are located below opposing sides of engagement feature 66 and which extend longitudinally alongside relatively thin wall section 306, and a pair of longitudinally extending grooves 376, which are formed in wall 307, which wall 307 is a distal extension of relatively thin wall section 306. The weakened areas formed by recesses 366 and grooves 376 can act as hinge features along either side of the wall section 306/307 that is slit apart by slitter tool 60, for example, to increase the ease of slitting.

FIGS. 4A and 5A further illustrate opposing flat wall sections 46 of inner surface 511 of relatively rigid part 111A of sealing assembly 30 extending within proximal port portion 101p of lumen 101. According to the illustrated embodiment, opposing flat wall sections 46 are distally offset from proximal opening 31 and are configured to serve as an internal engagement feature that interfaces with nose feature 638 of slitter tool 60 to act as a guide. Once blade 610 of tool 60 has slit through the proximal edge of relatively thin wall section 306 and, as the operator continues to pull proximal section 11 of catheter 100 proximally against blade 610, the guiding of nose 638 between flat wall sections 46 helps to prevent a lateral wandering of tool 60 and thereby maintain a relatively straight slitting path through catheter proximal section 11. Of course, various configurations of inner surface 511 within proximal port portion 101p, other than the illustrated flat wall sections 46, can form an internal engagement feature or guide for nose 638 of slitter, and are not outside the scope of the present invention. FIG. 6 further illustrates a secondary external engagement feature 67 which is formed in hub/relatively rigid second part 111B and located distal to external engagement feature 66, being approximately aligned with feature 66, for example, to help to further stabilize tool 60 as the operator continues slitting proximal section 11, distal of sealing assembly 30, since feature 636 of tool 60 will be constrained between opposing sides of feature 67. With reference back to FIG. 3A, secondary external engagement feature 67 may also serve as a visual cue to help orient sealing assembly 30 for insertion into hub/relatively rigid second part 111B of proximal section 11 of catheter 100.

FIG. 7A is a plan view of proximal section 11 of catheter 100 along with a syringe adapter tool 720 and a syringe 710, according to some embodiments. FIG. 7A illustrates adapter tool 720 including a distal tip segment 721, a proximal attachment segment 727, a feature 725 configured to interlock with external engagement feature 66 of proximal section 11, and a gripping segment 702 from which feature 725 extends in a cantilever fashion. Tool 720 is shown positioned/oriented for the insertion of distal tip segment 721 into proximal opening 31 of catheter lumen 101 and for the engagement of feature 725 with external engagement feature 66 of proximal section 11, for example, as illustrated in FIGS. 7B-C. Syringe 710 is shown positioned for attachment to tool 720, so that a tip 717 of syringe 710 can be inserted into a bore 729 of proximal attachment segment 727, for example, as illustrated in FIGS. 7B-C; thus, fluid from syringe can be injected into lumen 101 of catheter 100, through a channel 722 of distal tip segment 721, which is in fluid communication with bore 729. The location and configuration of gripping segment 702, between distal tip segment 721 and proximal attachment segment 727, allows an operator to grasp tool 720 for the aforementioned insertion of distal tip segment 721 into proximal opening 31 of catheter lumen 101 and the insertion of syringe tip 717 into bore 729 of tool 720.

FIG. 7A further illustrates tool including another feature 723 configured to interlock with an internal engagement feature of proximal section 11, such as opposing flat wall sections 46 (FIGS. 4A, 5A) within proximal port portion 101p of lumen 101. With reference to FIG. 7D, it may be seen that feature 723 includes relatively flat external surfaces located on either side of tool 720, each of which surface will face a corresponding flat wall section 46 of the internal engagement feature of proximal section 11, when interlocked therewith.

According to the illustrated embodiment, when features 725 and 723 interlock with respective external and internal engagement features 66 and 46 of catheter proximal end 11, distal tip segment 721 extends within lumen 101, to, and, preferably through seal zone portion 101s, as illustrated in the longitudinal section view of FIG. 7C. An outer diameter of distal tip segment is, thus, preferably sized to fit through seal zone portion 101s, and, according to some embodiments, may be sized for sealing engagement therein. Furthermore, the interlocking of one or both of features 725, 723 of tool 720 allows the operator to transfer a torsional force from the attached syringe 710 (FIGS. 7B-C) to catheter 100, through tool 720. Such capability gives the operator ability to simultaneously inject a contrast agent from syringe 710, through catheter lumen 101, and to maneuver catheter 100, via applied torque, in order to position the distal end 19 thereof (FIG. 2A) at a target location in a body of a patient. FIG. 7A further illustrates proximal attachment segment 727 of adapter tool 720 including an external feature 728 for mating with a luer lock 718 of syringe tip 717 in order to further secure the attachment of syringe 710 to tool 720 for torque transfer, according to some preferred embodiments.

With further reference to FIG. 7C, guide wire 200 is shown extending distally, from proximal portion 230 thereof, through tool 720 and into lumen 101. According to the illustrated embodiment, tool 720 further includes an instrument loading segment 726 to accommodate insertion of guide wire 200 into catheter 100. However, it should be noted that alternate embodiments of tool 720 need not include loading segment 726, in which case, guidewire 200 and/or another device/instrument could pass through seal zone portion 101s of lumen 101 alongside tool 720. FIG. 7D is a plan view of syringe adapter tool 720, according to some embodiments, wherein instrument loading segment 726 is shown including a passageway 724, which communicates with channel 722 of distal tip segment 721 and is accessible from an exterior of tool 720, so that distal tip 209 (FIGS. 1 and 9) of guide wire 200 may be inserted into channel 722, via passageway 724, and through seal zone portion 101s, via channel 722. An operator may desire to pass guide wire 200 through catheter and maneuver distal tip 209 thereof to a target site prior to loading and delivering a medical device, for example, medical electrical lead 600 (FIGS. 6 and 9), over guide wire 200. Absent any tool to set up a pathway through seal zone portion 101s, for example, channel 722, an operator may have some difficulty passing distal tip 209 of guide wire 200 through seal zone portion 101s, since distal tip 209 is preferably relatively floppy (to be atraumatic within the body of the patient) and deformable (to be shapeable in order to facilitate the steering thereof in the body). An operator may alternately pass a medical device, such as lead 600, through seal zone portion 101s and into catheter 100, without tool 720, prior to advancing guide wire 200 into catheter 100, in which case a lumen of the medical device provides the passageway through seal zone portion 101s for guide wire 200. Furthermore, the embodiment of tool 720 that includes loading segment 726 may facilitate insertion of the relatively large diameter guide wire 200', if the operator desires to insert catheter 100 before, or simultaneously with, the insertion of guide wire 200'.

FIG. 7D further illustrates distal tip segment 721 having a length $L_t$, which is, preferably, sufficient to reach through seal zone portion 101s, before tool 720 is fully inserted, so that at least a portion of passageway 724 is exposed proximal to proximal terminal end 113 of proximal section 11 for the insertion of guide wire distal tip 209. Once guide wire 200 has been passed in through passageway 724 and tool 720 is fully inserted, as illustrated in FIG. 7C, passageway 724 is positioned distal to proximal opening 31 so that exposed sealing area 123 can seal over passageway 724 to prevent leakage from lumen 101 of catheter 100 and from attached syringe 710, while allowing guide wire 200 to extend proximally out from passageway 724 and proximal opening 31. As previously described, in conjunction with FIGS. 3A-C and 5A, according to some preferred embodiments, exposed sealing area 123, as formed by soft part 311, extends into proximal port portion 101p of lumen 101 as relatively soft inner surface 201, which can provide additional sealing and strain relief at the interface between guide wire 200 and tool 720. With reference to FIGS. 7B-C, the location of external engagement feature 66 of catheter proximal section 11 opposite exposed sealing area 123, and the location of feature 725 of syringe adapter tool 720 opposite passageway 724 assure a proper orientation of passageway 724 toward exposed sealing area 123 (and relatively soft inner surface 201), for the above-described function, when features 725 interlocks with external engagement feature 66. FIG. 7D further illustrates tool 720 including an external surface 76 in which an optional groove 72 is formed; surface 76 and groove 72 are shown located just proximal to passageway 724 to receive that portion of guide wire 200 that extends just proximal to exposed sealing area.

With reference to FIGS. 7B-C, when syringe 710 is attached to catheter 100, via tool 720, an operator has the ability to inject a contrast agent from syringe 710 through catheter lumen 101 while applying torque to catheter 100 and/or maneuvering guide wire 200, for example, as was described above, to a target location. With reference back to the prior art system of FIG. 1, it may be appreciated that syringe 810 coupled to side tubing port 826 of sealing assembly 820, via stopcock 827, is a relatively bulky set up compared to the inline attachment of syringe 710, via tool 720, to proximal section 11 of catheter 100, and that this inline attachment can make the maneuvering of catheter 100, in conjunction with syringe injections, less cumbersome and more effective. Although guide wire 200 is described as the instrument whose insertion into catheter lumen 101 is facilitated by tool 720, passageway 724 and channel 722 may be sized to accommodate other types of instruments.

With further reference to FIG. 7D, distal tip segment 721 of syringe adapter tool 720 includes an optional slit 71 extending through a sidewall thereof, along length $L_t$ and between a distal opening into channel 722 and passageway 724. According to the illustrated embodiment, slit 71 allows guide wire 200 to pass therethrough, for example, by deformation of the sidewall of distal tip segment 721, in order to separate tool 720 from guide wire 200, which remains positioned within catheter 100 while tool 720 is pulled out from proximal section 11 of catheter 100. It should be noted that, tool 720 is preferably designed to be reusable, having relatively robust wall sections that will not permanently deform under repeated use, for example, during a procedure in which the operator needs to employ several guide wires in succession in order to reach the target site. According to an exemplary embodiment, tool 720 is formed from a polyether block amide such as Pebax®, or a polyolefin, such as Pro-fax polypropylene.

FIG. 8A is a perspective view of a syringe adapter tool 920, according to some alternate embodiments. FIG. 8A illustrates tool 920 having a configuration similar to tool 720, for example, in that tool 920 includes distal tip segment 721, gripping segment 702, proximal attachment segment 727, feature 725 configured to interlock with external engagement feature 66 of proximal section 11, and feature 723 configured to interlock with the internal engagement feature of catheter proximal section 11 (i.e. opposing flat wall sections 46). FIG. 8A also shows tool 920 including optional instrument loading segment 726 with passageway 724 for insertion of an instrument, such as guide wire 200, into channel 722 of distal tip segment 721, as described above for tool 720. Like adapter tool 720, adapter tool 920 is preferably designed to be reusable. In contrast to tool 720, tool 920 includes a sealing member 93, for example, formed from a relatively soft material, such as an LSR or a TPE, which may be over-molded onto a relatively rigid part 97 of tool 920, as will be described in greater detail below. FIG. 8A illustrates sealing member 93 extending distally from gripping segment 702 and including a sealing ring 934 and a lip 936.

FIG. 8B is an enlarged perspective view of tool 920 engaged with catheter proximal section 11 and syringe 710 attached to tool 920. With reference to FIGS. 8A-B, in conjunction with FIG. 7C, it may be appreciated that sealing ring 934 is positioned on tool 920 at a location for sealing within proximal port portion 101p of lumen 101, just distal to proximal opening 31, when tool 920 interlocks with catheter proximal section 11. FIG. 8B illustrates lip 936 abutting proximal terminal end 113 of catheter proximal section 11 along exposed sealing area 123, for example, to provide additional protection against backflow out from proximal opening 31 of lumen 101. FIGS. 8A-B further illustrate an optional groove 92 formed in sealing member 93 and extending longitudinally through ring 934 and lip 936 in order to better accommodate a proximal extension of an instrument, such as guide wire 200, that passes between sealing member 93 and exposed sealing area 123. However, it should be noted that the interface between the above-described relatively soft inner surface 201 of proximal port portion 101p and the relatively soft material (for example, one of the aforementioned CLS2000 LSR, Dynaflex™ G-6703 TPE, and Medalist® MD-100 TPE) that forms sealing member 93, at and around ring 934, can conform around the interposed instrument/guide wire so that groove 92 may not be necessary.

With further reference to FIG. 8A, tool 920 is shown divided into two relatively rigid parts 95 and 97, according to some preferred embodiments. FIG. 8A shows first part 95 forming a first portion of gripping segment 702 and feature 725, and shows second part 97 forming distal tip segment 721, optional loading segment 726, a second portion of gripping segment 702 and proximal attachment segment 727. According to some embodiments, sealing member 93 is over-molded onto second relatively rigid part 97 before attaching first relatively rigid part 95 to second part 97, for example, since the cantilever extension of feature 725 can interfere with such a molding operation. Part 97 may be formed from a polyether block amide such as Pebax®, or a polyolefin such as Pro-fax, while part 95 may be formed from an even more rigid material, for example, a polycarbonate, such as Makrolon 4258 (available from Bayer), or a co-polyester, such as Tritan MX731 (available from Eastman), for example, to strengthen feature 725 against deformation when feature 725 interlocks with external engagement feature 66 of catheter proximal section 11 and torsional forces are applied to tool 920. According to a first exemplary embodiment, part 97 is formed by Pebax® 7033 (available from Arkema) and sealing member 93 is formed by CLS2000 LSR (available from Momentive); and, according to a second exemplary embodiment, part 97 is formed by 6523 Pro-fax polypropylene (available from LyondellBasell Industries) and sealing member 93 is formed by either Dynaflex™ G-6703 TPE (available from GLS Corporation), or Medalist® MD-100 TPE (available from Teknor Apex).

Figure 9:
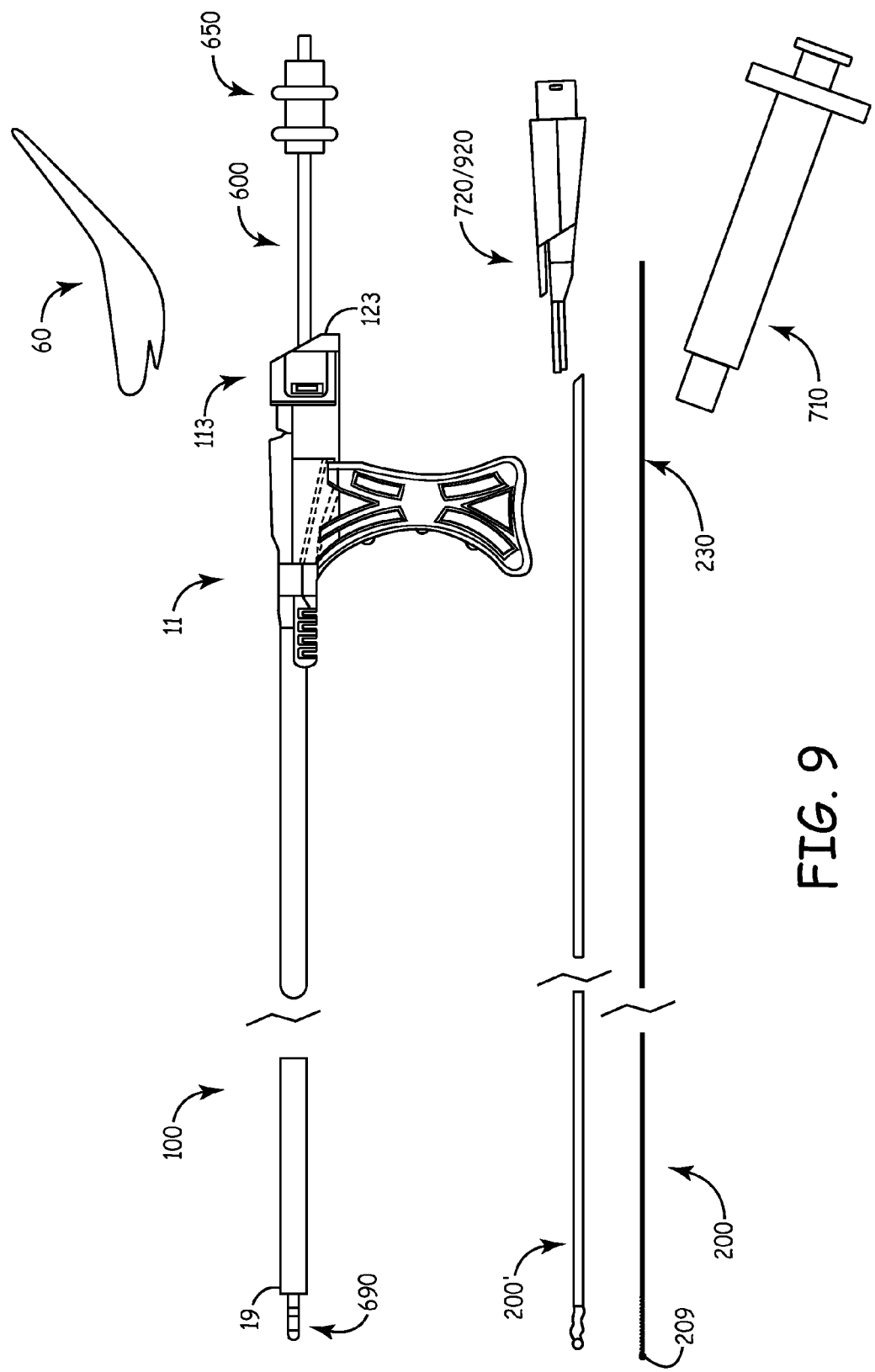
FIG. 9 is a plan view of a catheter delivery system, according to some embodiments of the present invention.

Finally, FIG. 9 is a plan view of a delivery system, wherein lead 600 is shown inserted within catheter 100. FIG. 9 illustrates the system including catheter 100, relatively smaller diameter guide wire 200, relatively larger diameter guide wire 200', syringe 710, syringe adapter tool 720/920 and slitter tool 60, for example, as have been described above. Although not shown, the system may further include one or more additional related accessories known in the art, which include, without limitation, additional guide wires, a dilator and a sub-selecting catheter. With reference to a sub-selecting catheter, it should be noted that such a catheter may have a proximal section including any or all of the features described above for proximal section 11, but that the sub-selecting catheter would necessarily include a smaller diameter tubular member (corresponding to tubular member 105 of catheter 100) in order to fit within catheter lumen 101. Catheter 100 and one or two of syringe adapter tool 720/920 may be packaged as a kit, which may also include any combination of one or more of the other related accessories mentioned above.

According to some methods of the present invention, an operator attaches syringe 710 to adapter tool 720/920 and inserts distal tip segment 721 of tool 720/920 into proximal opening 31 of catheter 100, for example, as illustrated in FIGS. 7B and 8B, and then purges catheter 100 of any air by flushing saline through lumen 101, prior to inserting catheter 100 into a body, for example, the venous system of a patient. As previously described, catheter 100 may be inserted over a pre-positioned relatively large diameter guide wire 200'. Once catheter 100 is inserted into the patient, the operator maneuvers catheter 100, by pushing and applying torque to proximal section 11, such that distal end 19 thereof is positioned, for example, in proximity to, or within the ostium of the patient's coronary sinus (CS Os). With reference back to FIGS. 7A-C and 8B, it may be appreciated that, according to preferred methods, the operator aligns feature 725 of tool 720/920 with external engagement feature 66 of catheter proximal section 11 in order to interlock feature 725 with feature 66, as distal tip segment 721 of tool 720/920 is being inserted through proximal opening 31 and into seal zone portion 101s of catheter lumen 101. According to the illustrated embodiment, feature 723 of tool 720/920 also interlocks with internal engagement feature 46 of catheter proximal section 11 (FIGS. 4A and 5A), upon insertion through proximal opening 31. The inline and interlocking attachment of syringe 710, via tool 720/920, with catheter proximal section 11, allows the operator to grasp the attached syringe 710 in order to maneuver catheter 100. Once distal end 19 of catheter 100 is positioned in general proximity to the CS Os, within the patient's right atrium, for example, being confirmed by fluoroscopic visualization of a radiopaque marker attached to catheter distal end 19, the operator may inject a radiopaque contrast agent from syringe 710, in order to better locate/visualize the CS Os, according to methods known in the art, while maneuvering catheter 100 to canulate the CS Os with catheter distal end 19, for example, by applying push and torque forces to catheter proximal section 11 while grasping syringe 710. It should be noted that a similar method may be used to position distal end 19 of catheter 100 in proximity to a target location along a wall of the atrium or along a right ventricular wall, for example, for subsequent site specific delivery of a medical instrument to the target location.

Once distal end 19 of catheter 100 is positioned, for example, within the CS Os, the operator may deliver lead 600 through catheter, either independent of guide wire 200, along with guide wire 200, which has been pre-loaded into lead 600, or over guide wire 200, so that distal tip 690 of lead 600, which may include one or more electrodes for electrical stimulation of the target site, is positioned distal to distal end 19 of catheter 100, as illustrated in FIG. 9. If lead 600 is to be delivered over guide wire 200, guide wire 200 may be inserted through seal zone portion 101s of lumen 101, with the aid of adapter tool 720/920, when adapter tool 720/920 includes loading segment 726. According to some methods, tool 720/920 is withdrawn just enough so that passageway 724 is exposed just proximal to catheter proximal opening 31 for the insertion of guide wire distal tip 209 therein and through channel 722 of distal tip segment 721, to pass through seal zone portion 101s of catheter lumen 101. Once catheter 100 and guide wire 200 are assembled together, for example, as illustrated in FIG. 7C, contrast agent may be injected from the attached syringe 710 while wire is maneuvered independently of catheter 100 and/or together with catheter 100, which operation may be facilitated by the inline and interlocking engagement of syringe 710 via tool 720/920. Once guide wire tip 209 is positioned, lead 600 may be loaded over proximal portion 230 of guide wire 200, for delivery thereover, after adapter tool 720/920 is completely withdrawn from catheter proximal section 11, as previously described, by passing proximal portion 230 of guide wire 200 through slit 71 in the sidewall of distal tip segment 721. Alternately, guide wire 200 may be loaded into lead 600, either before or after lead 600 is passed into catheter 100, through seal zone portion 101s, in which case, lead 600 itself facilitates passage of guide wire distal tip 209 through seal zone portion 101s. With reference back to FIGS. 4A and 5A and the description associated therewith, it may be appreciated that transition zone 513 facilitates the insertion of a relatively large instrument/device, for example, such as lead 600, through seal zone portion 101s of catheter lumen 101, without the need for a special insertion tool. As is also described above, once lead 600 is implanted, catheter 100 may be removed from around lead 600 by slitting, for example, with slitter tool 60.

In the foregoing detailed description of the disclosure, specific exemplary embodiments of the invention have been described. However, it may be appreciated that various modifications and changes can be made, without departing from the scope of the disclosure, as set forth in the appended claims.

We claim:

1. A catheter including a proximal section, a distal end and a lumen extending along a length of the catheter from the proximal section to the distal end, the proximal section of the catheter comprising:
   a proximal terminal end defining a perimeter of a proximal opening of the lumen; and
   a relatively soft part extending distally from the proximal opening of the lumen to a main portion of the lumen, the main portion extending distally to the distal end of the catheter;
   wherein the relatively soft part includes a distal face, adjacent to the main portion of the lumen, a slit and a bore, the bore including a proximal opening, a distal terminal end and a funnel-like segment that extends between the proximal opening and the distal terminal end of the bore and tapers down in size from a proximal diameter thereof to a distal diameter thereof, the distal terminal end of the bore being proximally offset from the distal face of the part, and the slit extending proximally through the part, from the distal face thereof and into the funnel-like segment, the slit having a size, or radial extent, that is greater than the distal diameter of the funnel-like segment of the bore;
   the slit and the bore of the relatively soft part form a seal zone portion of the lumen; and
   the soft part further forms only a portion of the perimeter of the proximal opening of the lumen.

2. The catheter of claim 1, wherein the bore of the soft part further includes a cylindrical segment extending between the distal diameter of the funnel-like segment and the distal terminal end of the bore, a diameter of the cylindrical segment being substantially constant along a length thereof and substantially equal to the distal diameter of the funnel-like segment.

3. The catheter of claim 2, wherein a diameter of the cylindrical segment is approximately 0.01 inch.

4. The catheter of claim 1, wherein the distal terminal end of the bore of the soft part is proximally offset from the distal face of the soft part by a distance of approximately 0.015 inch.

5. The catheter of claim 1, wherein the distal diameter of the funnel-like segment of the soft part is approximately 0.01 inch.

6. The catheter of claim 1, wherein the proximal diameter of the funnel-like segment of the soft part is approximately 0.05 inch.

7. The catheter of claim 1, wherein:
   the distal diameter of the funnel-like segment of the soft part is approximately 0.01 inch;
   the proximal diameter of the funnel-like segment is approximately 0.05 inch; and a length of the funnel-like segment, from the proximal diameter to the distal diameter, is approximately 0.05 inch.

8. The catheter of claim 7, wherein the slit of the soft part extends into the funnel-like segment of the soft part over a distance of approximately 0.025 inch.

9. The catheter of claim 1, wherein:
   the bore of the soft part further includes a transition zone extending between the proximal opening of the bore and the funnel-like segment;
   the transition zone tapers down in size from the proximal opening to the proximal diameter of the funnel-like segment.

10. The catheter of claim 1, wherein the proximal terminal end of the proximal section has a tapered profile and the portion of the perimeter of the proximal opening of the lumen formed by the soft part is exposed by virtue of the tapered profile.

11. The catheter of claim 1, wherein a central longitudinal axis of the bore of the soft part is radially offset from a central longitudinal axis of the proximal opening of the lumen.

\* \* \* \* \*